US007989599B2

(12) United States Patent
Suzuki et al.

(10) Patent No.: US 7,989,599 B2
(45) Date of Patent: Aug. 2, 2011

(54) ACTIVATOR INCLUDING BIOSURFACTANT AS ACTIVE INGREDIENT, MANNOSYL ERYTHRITOL LIPID, AND PRODUCTION METHOD THEREOF

(75) Inventors: Michiko Suzuki, Shiga (JP); Masaru Kitagawa, Osaka (JP); Shuhei Yamamoto, Fukui (JP); Atsushi Sogabe, Osaka (JP); Dai Kitamoto, Ibaraki (JP); Tomotake Morita, Ibaraki (JP); Tokuma Fukuoka, Ibaraki (JP); Tomohiro Imura, Ibaraki (JP)

(73) Assignees: Toyo Boseki Kabushiki Kaisha, Osaka (JP); National Institute of Advanced Industrial Science and Technology, Tokyo (JP)

( * ) Notice: Subject to any disclaimer, the term of this patent is extended or adjusted under 35 U.S.C. 154(b) by 166 days.

(21) Appl. No.: 12/367,870

(22) Filed: Feb. 9, 2009

(65) Prior Publication Data
US 2010/0228013 A1   Sep. 9, 2010

Related U.S. Application Data

(62) Division of application No. 12/376,805, filed on Feb. 9, 2009.

(51) Int. Cl.
*C07H 15/00* (2006.01)
*C12P 19/44* (2006.01)
*C07H 15/04* (2006.01)
*C07H 1/00* (2006.01)

(52) U.S. Cl. ......... 536/4.1; 536/115; 536/120; 536/124; 514/25; 435/74

(58) Field of Classification Search ................ 536/4.1, 536/115, 120, 124; 514/25; 435/74
See application file for complete search history.

(56) References Cited

U.S. PATENT DOCUMENTS
6,472,158 B1   10/2002   Vertesy et al.

FOREIGN PATENT DOCUMENTS

| EP | 1 964 546 | 9/2008 |
|---|---|---|
| JP | 57-145896 | 9/1982 |
| JP | 61-205450 | 9/1986 |
| JP | 62-084024 | 4/1987 |
| JP | 63-188697 | 8/1988 |
| JP | 03-141299 | 6/1991 |
| JP | 10-036279 | 2/1998 |
| JP | 10-045615 | 2/1998 |
| JP | 2002-293712 | 10/2002 |
| JP | 2003-040767 | 2/2003 |
| JP | 2006-261424 | 9/2003 |
| JP | 2004-075632 | 3/2004 |
| JP | 2005-068015 | 3/2005 |
| JP | 2005-089375 | 4/2005 |
| JP | 2005-104837 | 4/2005 |
| JP | 2005-325172 | 11/2005 |
| JP | 2006028069 A * | 2/2006 |
| WO | WO 2004/020647 | 3/2004 |
| WO | WO 2007/060956 | 5/2007 |

OTHER PUBLICATIONS

Morita, T., et al., "Characterization of the genus *Pseudozyma* by the formation of glycolipid biosurfactants, mannosylerythritol lipids", FEMS Yeast Research 7(2):286-292 (2007).
Crich et al. (2002) "Synthesis of the mannosyl erythritol lipid MEL A; confirmation of the configuration of the *meso*-erythritol moiety", Tetrahedron 58:35-44.
Konishi et al., (2007) "Production of different types of mannosylerythritol lipids as biosurfactants by the newly isolated yeast strains belonging to the genus *Pseudozyma*", Applied Microbiol. Biotech. 75:521-531.
Morita et al., (2007) "Microbial Conversion of Glycerol into Glycolipid Biosurfactants, Mannosylerythritol Lipids, by a Basidiomycete Yeast, *Pseudozyma antartica* JCM 10317", J. of Bioscience and Bioengineering 104(1):78-81.
Fukuoka et al., (2008) "A basidiomycetous yeast, *Pseudozyma crassa*, produces novel diastereomers of convential mannosylerythritol lipids as glycolipid biosurfactants", Carbohydrate Research, 343:2947-2955.
Kitamoto et al., (2002) "Functions and Potential Applications of Glycolipid Biosurfactants—from Energy-Saving Materials to Gene Delivery Carriers", J. of Biosc. And Bioeng., 94(3):187-201.
Haskins et al., (1955) "Metabolic Products of *Ustilago zeae* In Submerged Culture", Biochem. Of The Ustilaginales, 1: 749-756.
Deml et al., (1980) "Schizonellin A and B, New Glycolipids From *Schizonella melanogramma*", Phytochemistry 19:83-87.
Nakahara et al., (1983) "Induction and Characterization of Mutants Enhanced in Assimilability of *n*-Alkanes in Shake Cultures from a Strain of *Candida* sp.", Ferment. Technol. 61(1):19-23.
Kitamoto et al., (1990) "Extracellular Accumulation of Mannosylerythritol Lipids by a Strain of *Candida antartica*", Aric. Biol. Chem. 54(1):31-36.
Kim et al., (1999) "Characterization of a biosurfactant, mannosylerythritol lipid produced from *Candida* sp. SY16", Appl. Microbiol. Biotechnol. 52:713-721.
Kakugawa et al., (2002) "Isolation of Yeast Kurtzmanomyces sp. I-11, Novel Producer of Mannosylerythritol Lipid", Biosci. Biotechnol. Biochem. 66(1):188-191.
Kitamoto et al., (2003) "Production of Glycolipid Biosurfactants and Their Functional Development", Oleoscience (Japan), Japan Oil Chemists' Society 3:663-672.

(Continued)

Primary Examiner — Shaojia Anna Jiang
Assistant Examiner — Everett White
(74) Attorney, Agent, or Firm — Fish & Richardson P.C.

(57) ABSTRACT

The present invention includes as an active ingredient at least one biosurfactant, in particular mannosyl alditol lipid (such as MEL and MML) or triacylated mannosyl alditol lipid. This allows providing an activator and anti-aging agent that is excellent in activating and anti-aging effects on cells and that is safe enough to be used for a long time, and also providing cosmetics, quasi-drugs, drugs, and drinks and foods including the activator and the anti-aging agent as active ingredients. Further, the present invention provides MEL whose mannosyl erythritol skeleton in a molecular structure is 1-O-β-D-mannopyranosyl-meso-erythritol and a method for producing the MEL with use of a microorganism.

9 Claims, 15 Drawing Sheets

OTHER PUBLICATIONS

Imura et al., (2006) "Naturally Engineered Glycolipid Biosurfactants Leading to Distinctive Self-Assembled Structures", Chem. Euro. J. 12:2434-2440.

Kitamoto et al., (2000) "Formation of giant vesicles from diacylmannosylerythritols and their binding to concanavalin A", Chem. Commun. 861-862.

Inoh et al., (2001) "Biosurfactants of MEL-A Increase Gene Transfection Mediated by Cationic Liposomes", Biochemical and Biophysical Research Communications 289:57-61.

Kitamoto et al., (2001) "Microbial conversion of $n$-alkalines into glycolipid biosurfactants, mannosylerythritol lipids, by *Pseudozyma* (*Candida antartica*)", Biotech. Letters 23:1709-1714.

Kitamoto et al., (2001) "Remarkable Antiagglomeration Effect of a Yeast Biosurfactant, Diacylmannosylerythritol, on Ice-Water Slurry for Cold Thermal Storage", Biotchnol. Prog. 17:362-365.

Hong Im et al., (2001) "Mannosylerythritol lipid, a yeast extracellular glycolipid, shows high binding affinity towards human immunoglobulin G", 1:5.

Inoh et al., (2004) "Biosurfactant MEL-A dramatically increases gene transfection via membrane fusion", Elsevier J. of Controlled Release 94:423-431.

Igarashi et al., (2006) "Biosurfactant MEL-A enhances cellular association and gene transfection by cationic liposome", Elsevier J. of Controlled Release 362-368.

Ueno et al., (2007) "Characterization of Biosurfactant-Containing Liposomes and Their Efficiency for Gene Transfection", Biol. Pharm., Bull. 30(1):169-172.

S. Lang, (2002) "Biological amphiphiles (microbial biosurfactants)", Current Opinion in Colloid & Interface Science 7:12-20.

Kurz, et al., "Ustilipids, Acylated β-D-Mannopyranosyl D-Erythritols from *Ustilago maydis and Geotrichum candidum*", The Journal of Antibiotics, vol. 56 No. 2, Feb. 2003.

Kitamoto, et al., "Formation of giant vesicles from diacylmannosylerythritols, and their binding to concanavalin A", Chem. Commun., 2000, 861-862.

Fukuoka, et al., "A basidiomycetous yeast, *Pseudozyma crassa*, produces novel diastereomers of conventional mannosylerythritol lipids as glycolipid biosurfactants", Carbohydrate Research, 343 (2008) 2947-2955.

* cited by examiner

FIG. 7
MEL-B (produced by P. tsukubaensis)
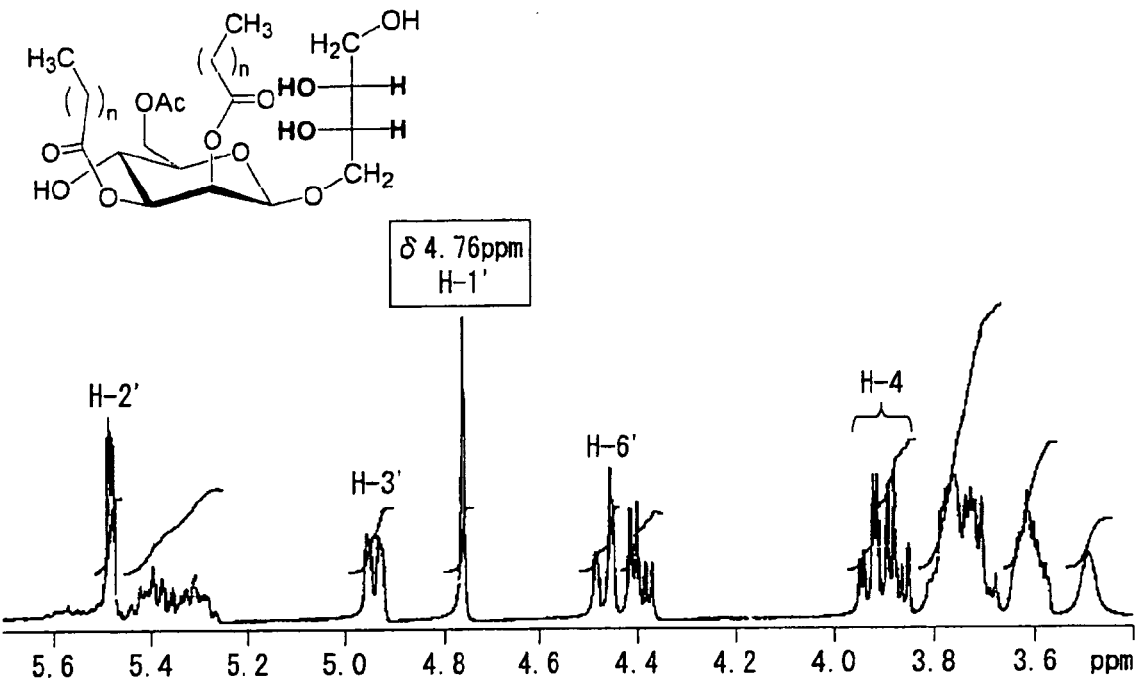
MEL-B (produced by P. antarctica)
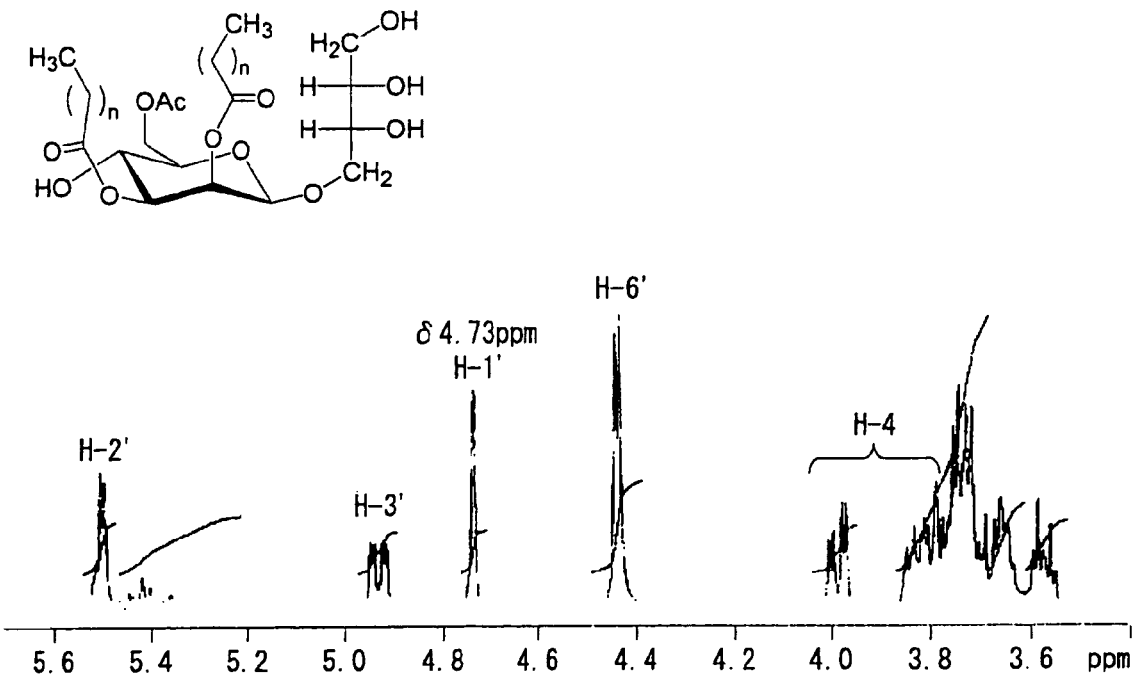

FIG. 8
ME(P. tsukubaensis)
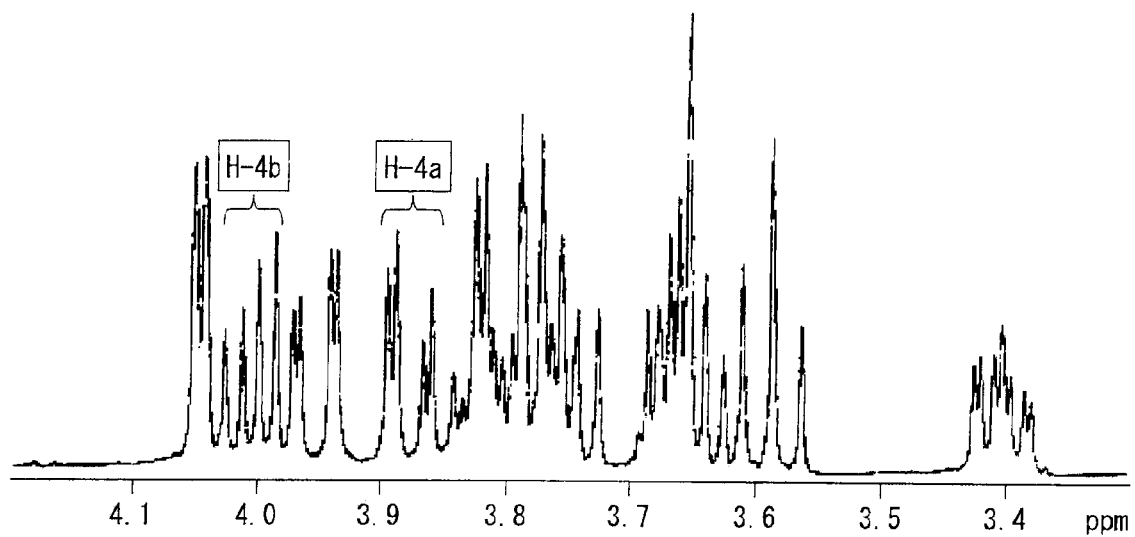
ME(P. antarctica T-34)
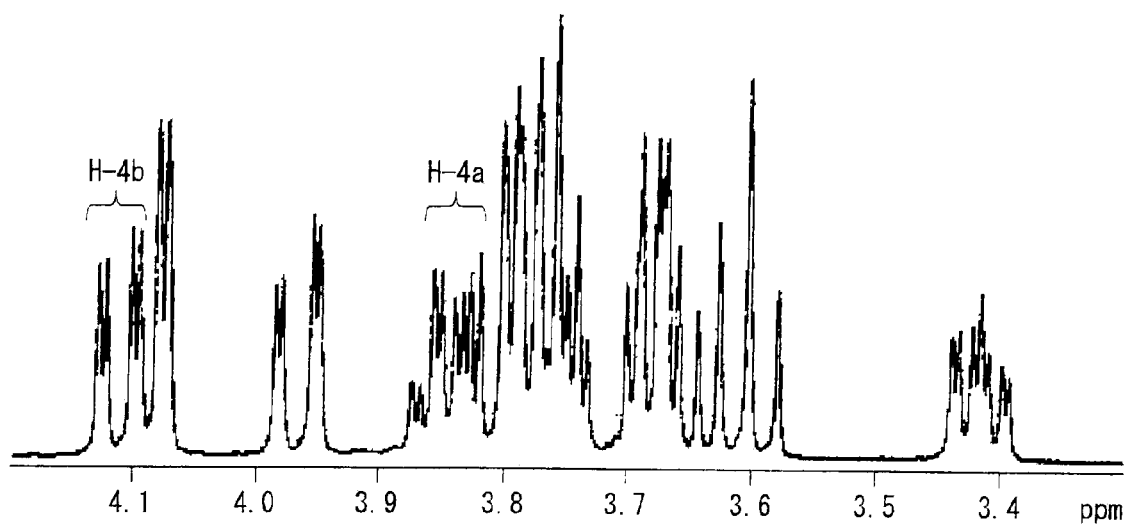

FIG. 10
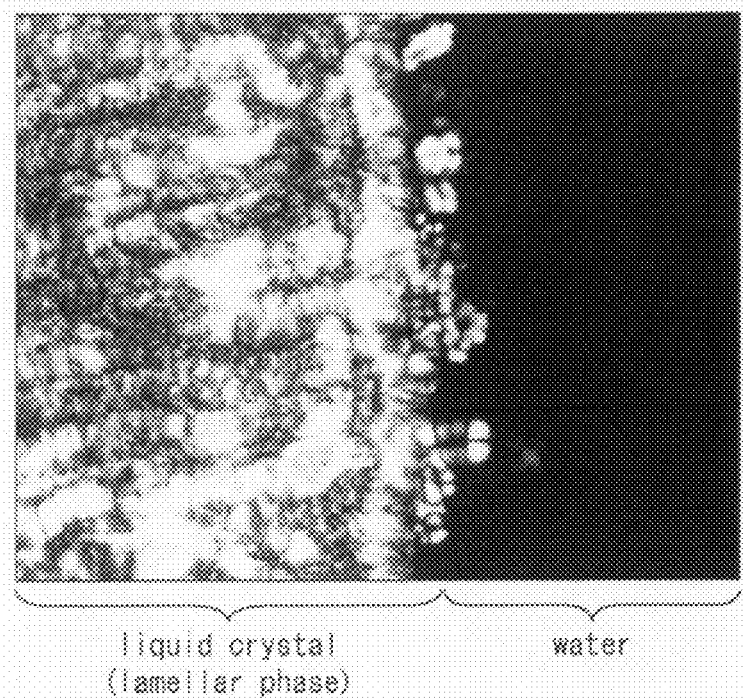
MEL produced by P. tsukubaensis
liquid crystal (lamellar phase) — water
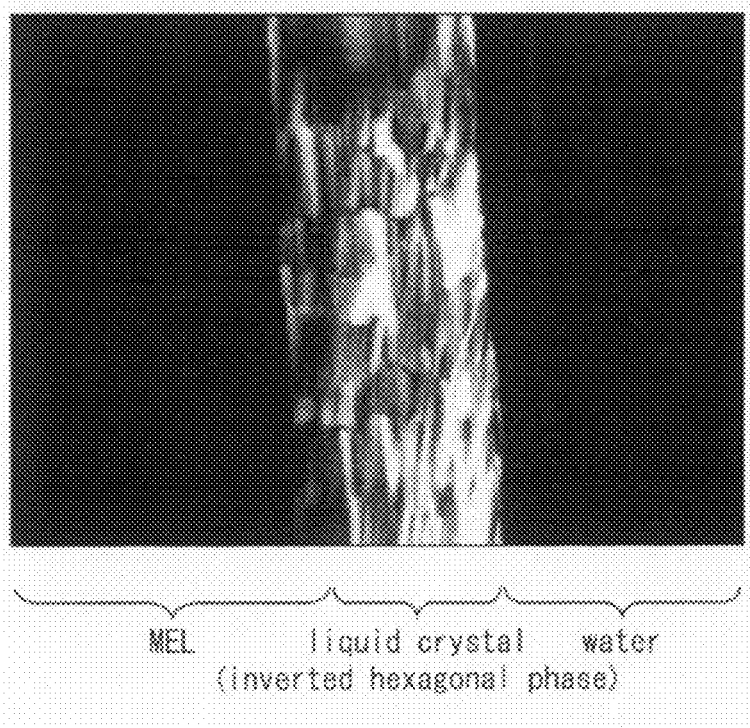
MEL produced by P. antarctica
MEL — liquid crystal (inverted hexagonal phase) — water FIG. 11
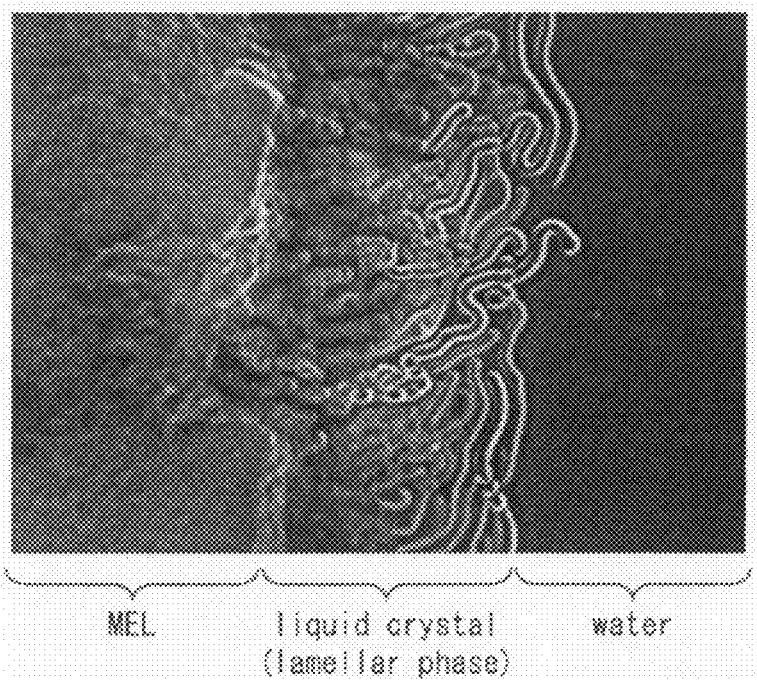
MEL produced by P. tsukubaensis
MEL | liquid crystal (lamellar phase) | water
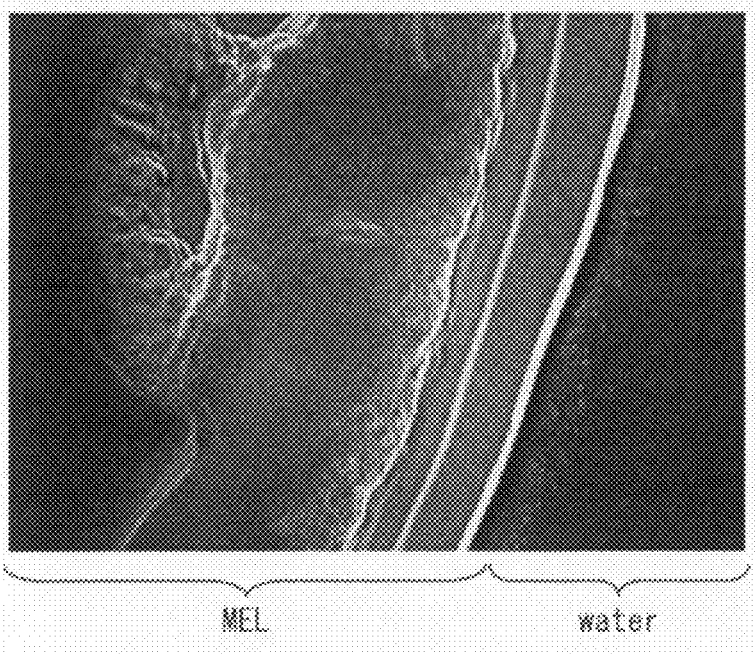
MEL produced by P. antarctica
MEL | water

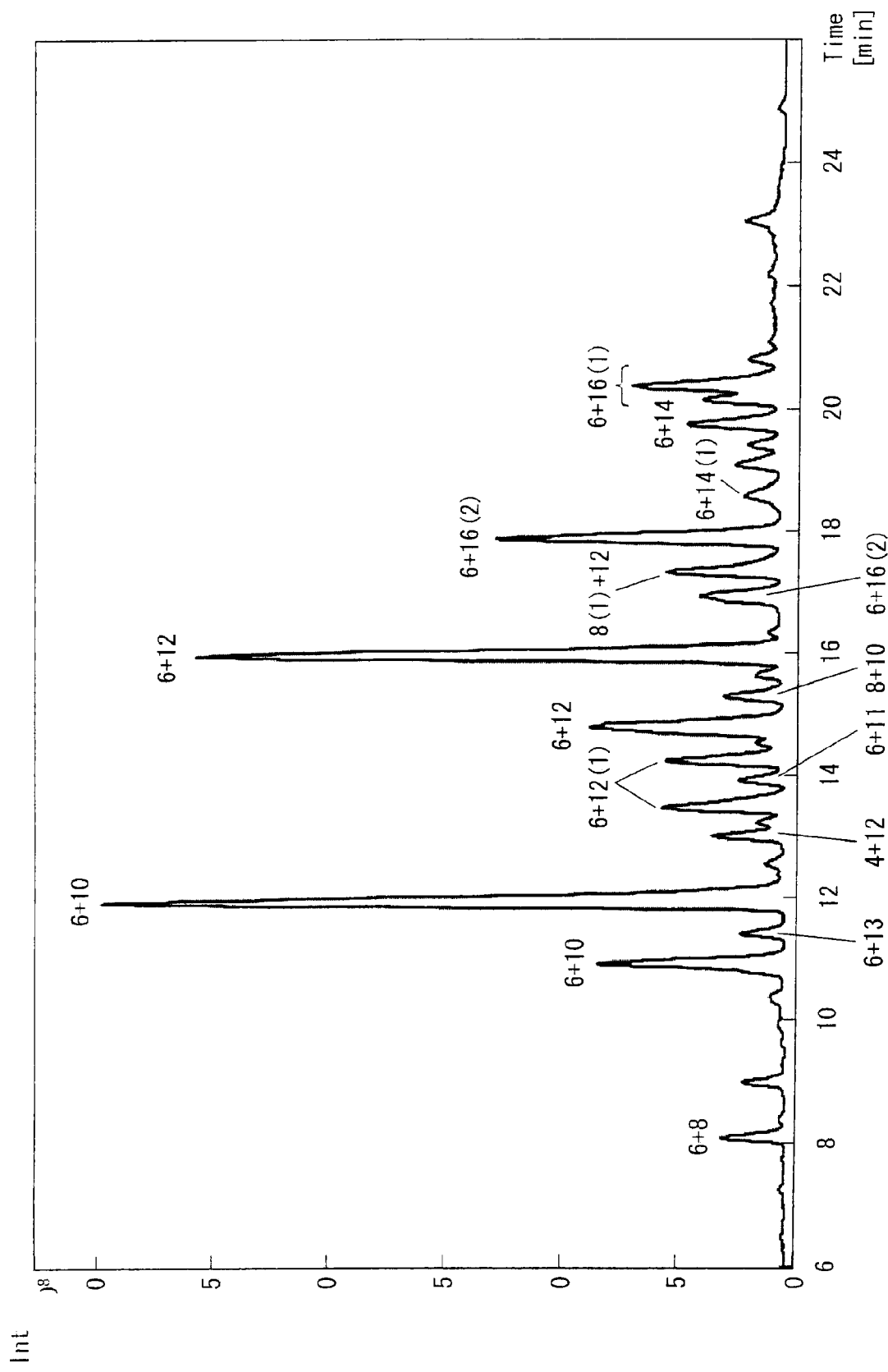

ACTIVATOR INCLUDING BIOSURFACTANT AS ACTIVE INGREDIENT, MANNOSYL ERYTHRITOL LIPID, AND PRODUCTION METHOD THEREOF

This application is a divisional application of U.S. application Ser. No. 12/376,805, filed Feb. 9, 2009, which is a National Stage entry of PCT/JP2007/065427 filed Aug. 7, 2007, which claims priority to Japanese Application Serial Nos. 2007-179892 filed Jul. 9, 2007 and 2006-219170 filed Aug. 11, 2006. The contents of each of the foregoing applications are incorporated by reference herein.

TECHNICAL FIELD

The present invention relates to an activator including a biosurfactant as an active ingredient. In particular, the present invention relates to cosmetics, quasi-drugs, drugs, drinks and foods, each including a biosurfactant which activates various cells and is effective for anti-aging, hair growth, and prevention of loss of hair.

Further, the present invention relates to new mannosylerythritol lipid (which may be hereinafter referred to as MEL) and a production method thereof. To be specific, the present invention relates to: an MEL which is one of glycolipids produced by microorganism and whose mannosylerythritol skeleton in a molecular structure is 1-O-β-D-mannopyranosyl-meso-erythritol; and a production method of the MEL by microorganism.

BACKGROUND ART

Aging of individuals and various diseases due to the aging are greatly involved with aging of all dividing cells (drop of dividing speed, drop of cell function). For example, skin includes epidermic cells, fibroblasts, and extracellular matrixes for supporting skin structures other than these cells, such as elastion and collagen. In young skin, interactivities between these skin tissues maintain homeostasis, which keeps moisture, flexibility, and resiliency. Consequently, skin appears to have tension and smoothness, and is kept fresh. However, aging, ultra-violet ray, dryness, stress etc. decrease functions of extracellular matrixes and fibroblasts in particular. Consequently, flexibility of skin and moisture-keeping function of skin drop, skin loses tension and smoothness, and senile symptoms such as chaps, wrinkles, and somberness appear.

In order to stop or prevent aging in cell level, activators and anti-aging agents have been searched. Known examples of activators derived from animals include hydrolysis of connective tissue (Patent Document 1), water-soluble protein derived from thymus gland and spleen (Patent Document 2), and essence of bovine placenta (Patent Document 3). Known examples of activators derived from plants include sesame, Chinese yam, pepper, *angelica acutiloba*, houttuynia, mondo grass (Patent Document 4), almond, *taraxacum officinale*, elder, *Cnidium officinale, swertia japonica, morus ihou*, inner core of seed of peach, ginseng, hop, althaea, and Job's tears. A part of these is used as an activator and an anti-aging agent in quail-drugs and cosmetics. However, an activator and an anti-aging agent that show satisfactory working effects are not yet obtained.

Mannosylerythritol lipid (MEL) is a natural surfactant produced by yeast, and it is reported that MEL has various physiological functions (Non-patent Document 1). Further, recently, mannosylmannitol lipid (MML) in which erythritol is replaced with mannitol has been found (Patent Document 9). As for usage as external medicines and cosmetics, effectiveness as an anti-inflammatory agent and an anti-allergy agent (Patent Document 10) and baldness remedy and hair growth (Patent Document 11), an anti-bacterial effect (Patent Document 12), and surface-tension-reduction function (Patent Document 13) are known.

However, activating function of MEL for cells has been completely unknown. Further, hair growth function described in Patent Document 11 was confirmed through animal experiments, and it has not been reported that MEL activates human head hair-papilla cells.

As described above, it is reported that a biosurfactant such as glycolipid has environment-friendly features such as high biodegradability and low toxicity, and has new physiological functions. In view of these features, widely applying a biosurfactant to food industry, cosmetic industry, medicine industry, chemical industry, and field of environment allows attaining a sustainable society and providing high-function products, and therefore very significant.

One of representative glycolipid biosurfactants is MEL. MEL is a material found from *Ustilago nuda* and *Shizonella melanogramma* (see Non-patent Documents 2 and 3). Later, it is reported that MEL can be produced by yeasts such as *Candida* yeast that is a mutated strain producing itaconic acid (see Patent Document 14 and Non-patent Document 4), *Candida antarctia* (currently called as *Pseudozyma antarctica*) (see Non-patent Documents 5 and 6), and *Kurtzmanomyces* yeast (see Non-patent Document 7). Nowadays, long-time continuous cultivation and production allows producing 300 g/L or more of MEL.

[Patent Document 1]
Japanese Unexamined Patent Publication No. Tokukaisho 62-84024
[Patent Document 2]
Japanese Unexamined Patent Publication No. Tokukaisho 63-188697
[Patent Document 3]
Japanese Unexamined Patent Publication No. Tokukaihei 03-141299
[Patent Document 4]
Japanese Unexamined Patent Publication No. Tokukaihei 10-45615
[Patent Document 5]
Japanese Unexamined Patent Publication No. Tokukaihei 10-036279
[Patent Document 6]
Japanese Unexamined Patent Publication No. Tokukaihei 10-36279
[Patent Document 7]
Japanese Unexamined Patent Publication No. Tokukai 2004-75632
[Patent Document 8]
Japanese Unexamined Patent Publication No. Tokukai 2005-89375
[Patent Document 9]
Japanese Unexamined Patent Publication No. Tokukai 2005-104837
[Patent Document 10]
Japanese Unexamined Patent Publication No. Tokukai 2005-68015
[Patent Document 11]
Japanese Unexamined Patent Publication No. Tokukai 2003-261424
[Patent Document 12]
Japanese Unexamined Patent Publication No. Tokukaisho 57-145896

[Patent Document 13]
Japanese Unexamined Patent Publication No. Tokukaisho 61-205450
[Patent Document 14]
Japanese Unexamined Patent Publication No. Tokukosho 57-145896
[Non-patent Document 1]
Journal of bioscience and bioengineering, 94, 187 (2002)
[Non-patent Document 2]
R. H. Haskins, J. A. Thorn, B. Boothroyd, Can. J. Microbiol., Vol 1, p749-756, 1955.
[Non-patent Document 3]
G. Deml, T. Anke, F. Oberwinkler, B. M. Giannetti, W. Steglich, Phytochemistry, Vol 19, p 83-87, 1980.
[Non-patent Document 4]
T. Nakahara, H. Kawasaki, T. Sugisawa, Y. Takamori, T. Tabuchi, J. Ferment. Technol. Vol61, p19-23, 1983.
[Non-patent Document 5]
D. Kitamoto, S. Akiba, C. Hioki, T. Tabuch, Agric. Biol. Chem., Vol 54. P31-36, 1990.
[Non-patent Document 6]
H.-S. Kim, B.-D. Yoon, D.-H. Choung, H.-M. Oh, T. Katsuragi, Y. Tani, Appl. Microbiol. Biotechnol., Springer-Verlag, Vol52, p713-721, 1999.
[Non-patent Document 7]
K. kakukawa, M. Tamai, K. Imamura, K. Miyamoto, S. Miyoshi, Y. Morinaga, O, Suzuki, T. Miyakawa, Biosci. Biotechnol. Biochem., Vol66, p188-191, 2002.
[Non-patent Document 8]
D. Crich, M. A. Mora, R. Cruz, Tetrahedron, Elsevier, Vol58, p35-44, 2002.
[Non-patent Document 9]
Dai Kitamoto, Oleoscience (Japan), Japan Oil Chemists' Society, Vol. 3, p663-672 (2003).
[Non-patent Document 10]
T. Imura, N. Ohta, K. Inoue, N. Yagi, H. Negishi, H. Yanagishita, D. Kitamoto, Chem. Eur. J, Wiley, Vol12, p2434-2440, 2006.

DISCLOSURE OF INVENTION

It is an extremely important object to carry out activation and anti-aging of mammals, in particular, humans. Although various activating materials and anti-aging agents derived from animals and plants have been discovered, there has not been yielded an effect that is so sufficient and stable as to allow industrial use of the activating materials and the anti-aging agents, and new activating materials and anti-aging agents have been searched.

Therefore, an object of the present invention is to provide an activator and anti-aging agent that are excellent in an activating effect and an anti-aging effect on cells and are safe enough to be used for a long time. The other object of the present invention is to provide cosmetics, quasi-drugs, drugs, and drinks and foods each including the activator and the anti-aging agent as active ingredients.

Further, as described above, in order that a biosurfactant that has environment-friendly features such as high biodegradability and low toxicity and that has new physiological functions is used in food industry, cosmetic industry, medicine industry, chemical industry, field of environment etc., it is necessary to increase production efficiency of the biosurfactant and to widen the variety of a structure and a function of the biosurfactant. In particular, MEL is excellent not only in productivity and surface properties but also in specific self-assembling property and bioactivity, and various applications of MEL have been developed by taking advantage of the specific self-assembling property and bioactivity.

However, microorganism-derived MEL having been reported so far has a sugar skeleton that is 4-O-β-D-mannopyranosyl-meso-erythritol structure. Therefore, widening the variety of a structure and a function of MEL has been strongly requested.

In particular, chirality of molecule of an organic compound having bioactivities is very important point. It has been reported that MEL has various bioactivities such as antibacterial activity, anti-tumor property, and glycoprotein binding ability (Non-patent Document 9). Further, MEL shows a very unique self-assembling property, and application of MEL to a liposome material and a liquid crystal technique is tried by taking advantage of the self-assembling property. It is reported that a slight difference in a molecular structure has a great influence on formation of a self-assembling body (Non-patent Documents 9 and 10).

In view of the above, it is expected that producing a large amount of optical isomers of conventionally known MEL and comparing properties of the optical isomers and evaluating functions of the optical isomers would greatly contribute to development of applications of MEL.

Non-patent Document 8 describes that MEL having 1-O-β-D-mannopyranosyl-meso-erythritol structure was chemically synthesized. According to the description, only one MEL is synthesized through a very complex process and therefore the synthesis lacks versatility and is difficult to use.

In another aspect, the present invention was made in view of the foregoing problem, and an object of the present invention is to provide: MEL having 1-O-β-D-mannopyranosyl-meso-erythritol structure, that is an optical isomer of conventional MEL having 4-O-β-D-mannopyranosyl-meso-erythritol structure; and a production method thereof.

The inventors of the present invention have diligently studied in order to achieve the foregoing objects, and found that MEL and triacyl MEL are effective for activating cells, and thus completed the present invention. Further, the inventors of the present invention have diligently studied in order to achieve the foregoing objects, and found microorganism that produces MEL having 1-O-β-D-mannopyranosyl-meso-erythritol structure (which may hereinafter referred to as "MEL of the present invention" or "1-O-MEL"), which is an optical isomer of conventional MEL having 4-O-β-D-mannopyranosyl-meso-erythritol structure (which may be hereinafter referred to as "conventional MEL" or "4-O-MEL"), and thus completed the present invention. That is, the present invention includes the following subject matters.

(1) An activator, including a biosurfactant as an active ingredient.

(2) The activator as set forth in (1), wherein the biosurfactant is mannosylalditol lipid or a triacyl derivative of mannosylalditol lipid.

(3) The activator as set forth in (2), wherein the mannosyl alditol lipid is mannosylerythritol lipid (MEL) or mannosylmannitol lipid (MML).

(4) An anti-aging agent, including as an active ingredient an activator as set forth in any one of (1) to (3).

(5) A hair growth agent, including as an active ingredient an activator as set forth in any one of (1) to (3).

(6) An external agent, including as an active ingredient one of an activator as set forth in any one of (1) to (3), an anti-aging agent as set forth in (4), and a hair growth agent as set forth in (5).

(7) A cosmetic, including as an active ingredient one of an activator as set forth in any one of (1) to (3), an anti-aging agent as set forth in (4), and a hair growth agent as set forth in (5).

(8) A quasi-drug, including as an active ingredient one of an activator as set forth in any one of (1) to (3), an anti-aging agent as set forth in (4), and a hair growth agent as set forth in (5).

(9) A drug, including as an active ingredient one of an activator as set forth in any one of (1) to (3), an anti-aging agent as set forth in (4), and a hair growth agent as set forth in (5).

(10) Food and drink, including as an active ingredient one of an activator as set forth in any one of (1) to (3), an anti-aging agent as set forth in (4), and a hair growth agent as set forth in (5).

(11) Mannosylerythritol lipid, including a structure represented by formula (1)

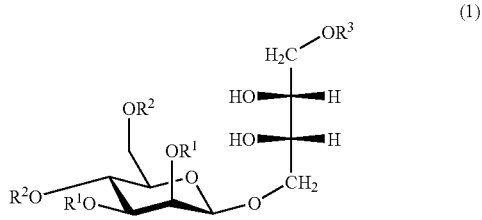

(1)

wherein substituents $R^1$ may be a same as each other or different from each other and represent fatty series acyl groups having 4-24 carbon atoms, substituents $R^2$ may be a same as each other or different from each other and represent hydrogen or acetyl groups, and a substituent $R^3$ represents hydrogen or a fatty series acyl group having 12 carbon atoms, excluding a structure wherein the substituents $R^1$ are fatty series acyl groups having 12 carbon atoms, the substituents $R^2$ are acetyl groups, and the substituent $R^3$ is hydrogen.

(12) The mannosylerythritol lipid as set forth in (11), wherein in the formula (1), one of the substituents $R^2$ is an acetyl group and the other of the substituents $R^2$ is hydrogen.

(13) The mannosylerythritol lipid as set forth in (11) or (12), wherein in the formula (1), the substituent $R^3$ is a fatty series acyl group having 2-24 carbon atoms.

(14) The mannosylerythritol lipid as set forth in any one of (11)-(13), the mannosylerythritol lipid being produced by microorganism.

(15) A method for producing mannosylerythritol lipid, comprising the steps of culturing microorganism that belongs to *Pseudozyma* genus and that is capable of producing mannosylerythritol lipid, so as to produce mannosylerythritol lipid including a structure represented by formula (1)

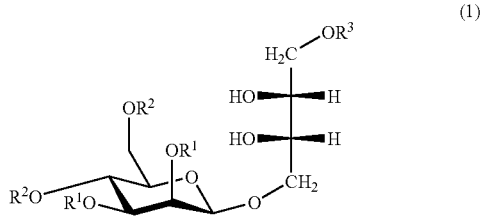

(1)

wherein substituents $R^1$ may be a same as each other or different from each other and represent fatty series acyl groups having 4-24 carbon atoms, substituents $R^2$ may be a same as each other or different from each other and represent hydrogen or acetyl groups, and a substituent $R^3$ represents hydrogen or a fatty series acyl group having 2-24 carbon atoms.

(16) The method as set forth in (15), wherein the microorganism is one of *Pseudozyma tsukubaensis* and *Pseudozyma crassa*.

The biosurfactant used as an active ingredient in the activator of the present invention has a notable activating function on various cells. Therefore, the activator of the present invention yields an excellent effect as an anti-aging agent and a hair-growth agent. further, the biosurfactant is a natural surfactant derived from living organism and therefore has highly safe, which yields an effect that the activator of the present invention can be sufficiently used for a long time. Further, the biosurfactant can be produced by culturing microorganism. Therefore, the costs for the raw material of the bio surfactant is low and a large number of the biosurfactant can be produced. This yields an effect that the activator of the present invention can be provided in a low price.

Moreover, the MEL of the present invention is an optical isomer of conventionally known MEL. Difference in chirality of molecules has great influence on physiological activity and a self-assembling body forming function. Consequently, although there is no difference in surface activity between the MEL of the present invention and the conventional MEL, other properties of the MEL of the present invention are different from those of the conventional MEL. Therefore, comparison of the MEL of the present invention with the conventional MEL in terms of their physical properties and evaluation of functions of the MEL of the present invention make important contributions to development in the usage of MEL. In particular, the MEL of the present invention has a liquid crystal forming ability which is different from that of conventional MEL.

Further, with the production method of MEL of the present invention, it is possible to easily produce a large number of an optical isomer of conventionally known MEL.

Additional objects, features, and strengths of the present invention will be made clear by the description below. Further, the advantages of the present invention will be evident from the following explanation in reference to the drawings.

BRIEF DESCRIPTION OF DRAWINGS

FIG. 7 is an enlarged drawing (3.4-5.7 ppm) of a sugar skeleton part in $^1$H-NMR spectrum of MEL produced by *Pseudozyma tsukubaensis* JCM 10324 strain and *Pseudozyma antarctica* KM-34 (FERMP-20730) strain.

FIG. 8 is an enlarged drawing (3.3-4.2 ppm) of a sugar skeleton part in $^1$H-NMR spectrum of mannosylerythritol synthesized from a starting material that is MEL produced by *Pseudozyma tsukubaensis* JCM 10324 strain and *Pseudozyma antarctica* KM-34 (FERMP-20730) strain.

FIG. 10 is a drawing showing the result of polarization microscope observation of liquid crystal forming ability of MEL produced by *Pseudozyma tsukubaensis* JCM 10324 strain and *Pseudozyma antarctica* KM-34 (FERMP-20730) strain, the liquid crystal forming ability being evaluated by a water-invading method.

FIG. 11 is a drawing showing the result of polarization microscope observation of liquid crystal forming ability of MEL produced by *Pseudozyma tsukubaensis* JCM 10324 strain and *Pseudozyma antarctica* KM-34 (FERMP-20730) strain, the liquid crystal forming ability being evaluated by a water-invading method.

FIG. 15 is a drawing illustrating the result of lipid domain analysis by HPLC (ODS)-MS analysis of triacyl MEL produced by *Pseudozyma hubeiensis*.

BEST MODE FOR CARRYING OUT THE INVENTION

Embodiment 1

<1. Activator>

Figure 1:
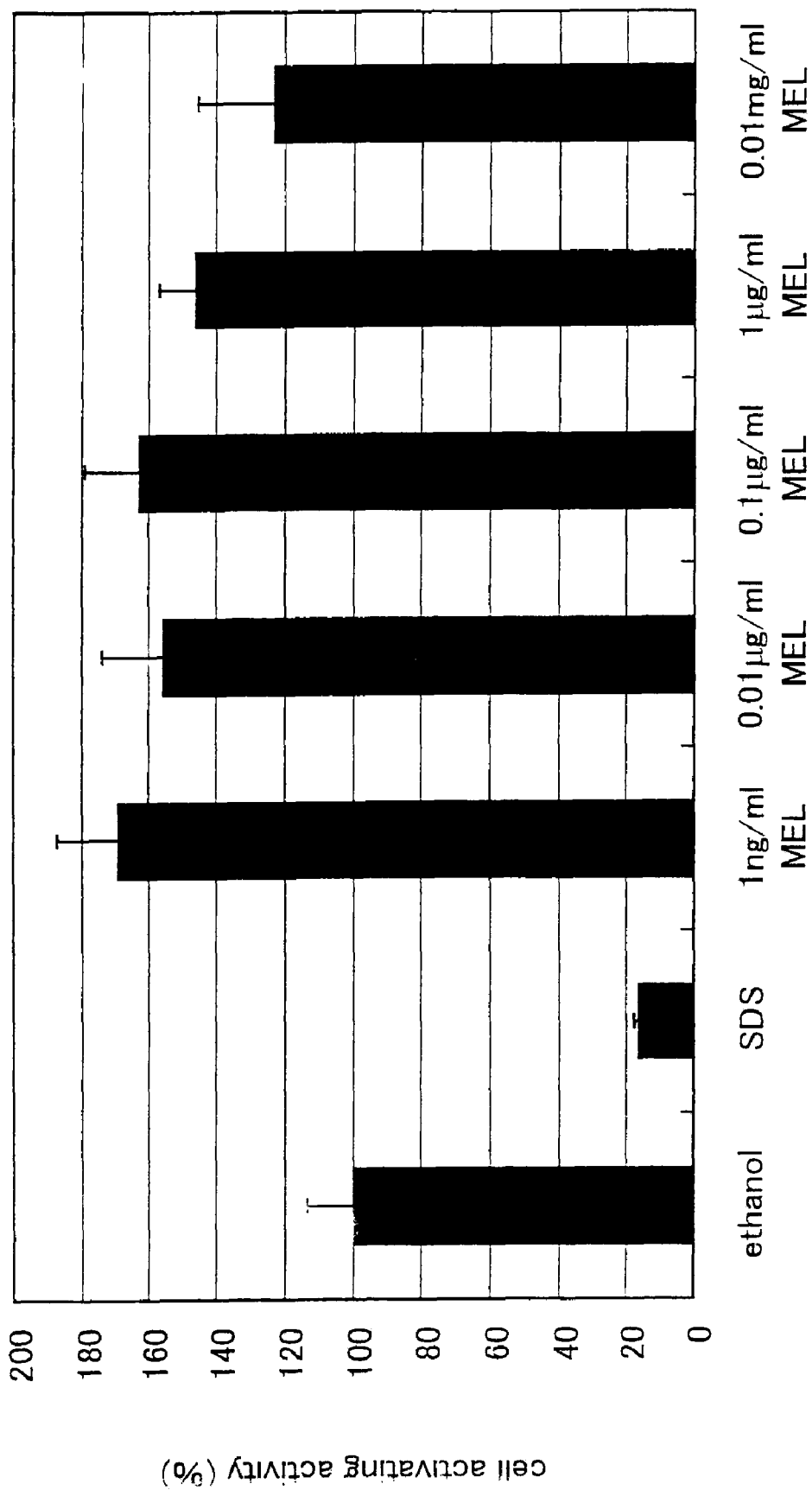
FIG. 1 is a graph showing the result of examining a cell-activating function of MEL (MEL-A produced from soybean oil) on normal human skin fibroblasts.

"Activating" in the present specification indicates maintaining or prompting cell functions or cell activities. Consequently, it is possible to prevent the drops of the cell functions or cell activities, i.e. it is possible to prevent aging of cells. Therefore, "activator" is synonymous to "cell activator", and is effective as "anti-aging agent".

For example, "activating" and "anti-aging" in skin cells indicate reducing drop of functions of the skin cells due to accumulation of structural change of basement membrane derived from aging and photoaging, thereby preventing or improving wrinkles, sags, hardening etc. of skins, so as to maintain resilient, young, and healthy skins. Further, in a case of hair-papilla cells or hair matrix cells, "activating" and "anti-aging" indicates reducing drop of functions of hair-papilla cells or hair matrix cells due to aging, stress, and hormone balance, thereby keeping hair cycle so as to prevent loss of hair.

"Biosurfactant" is a general term for a substance that is produced by living organisms and that has a surfactant property and an emulsification property. The biosurfactant not only includes an excellent surfactant property and a high emulsification property, but also includes various physiological functions, which may attain behaviors and functions other than those of a synthesized surfactant. The biosurfactant can be mass-produced through cultivation of microorganism, and may be used as a premixed product.

"Premixed product" is a product obtained by adding a dispersing agent to a functional material or by diluting the functional material with use of a solvent so as to be usable when producing cosmetics.

Examples of the bio surfactant include mannosylerythritol lipid (MEL), mannosylmannitol lipid (MML), trehaloselipid, rhamnolipid, sophorose lipid, surfactin, spiculisporic acid, and emulsan. These examples can be used in the activator of the present invention. Among them, it is preferable to use a biosurfactant having a lamellar structure, and it is particularly preferable to use MEL and MML.

Four kinds of MEL are known according to whether an acetyl group at 4- and 6-positions of mannose exists or not. The four kinds include MEL-A, MEL-B, MEL-C, and MEL-D. Chemical formula (2) shows a structure of MEL-A. In chemical formula (2), R1 and R2 indicate carbon hydride groups. That is, MEL-A includes alkanoyl groups having 5-19 carbon atoms at 2- and 3-positions of mannose and acetyl groups at 4- and 6-positions of mannose in chemical formula (2). MEL-B includes H instead of an acetyl group ($CH_3CO$) at the 4-position of mannose in chemical formula (2). MEL-C includes H instead of an acetyl group ($CH_3CO$) at the 6-position of mannose in chemical formula (2). MEL-D includes H instead of acetyl groups ($CH_3CO$) at the 4- and 6-positions of mannose in chemical formula (2).

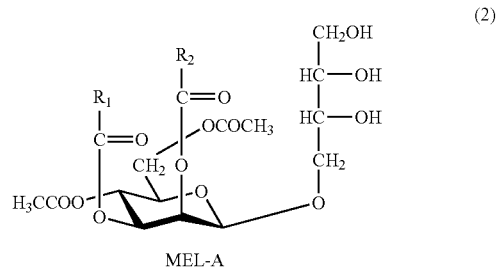

MEL-A (2)

Chemical formula (3) indicates a structure of MML. In chemical formula (3), R1 and R2 indicate carbon hydride groups. Further, in chemical formula (3), at least one of or both of acetyl groups ($CH_3CO$) at the 4- and 6-positions of mannose may be replaced with H.

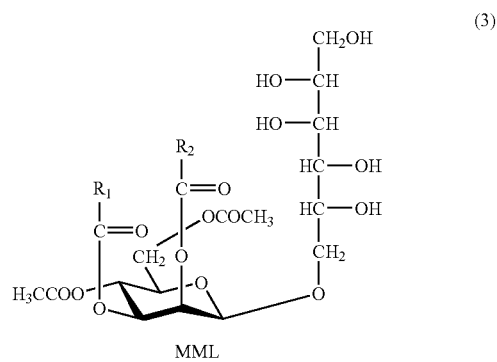

MML (3)

The biosurfactant used in the activator of the present invention may be a tryacyl derivative of MEL or a tryacyl derivative of MML. The tryacyl derivative of biosurfactant is a biosurfactant having a new structure with higher hydrophobicity than that of MEL or MML. For example, in a case of obtaining a large amount of the bio surfactant from other than a culture solution of MEL-producing bacteria, it is possible to produce the biosurfactant by reacting MEL with various plant oils with use of enzymes.

Triacyl derivative of MEL, i.e. triacylmannosylerythritol lipid (which may be referred to as triacyl MEL) includes a structure shown by chemical formula (4).

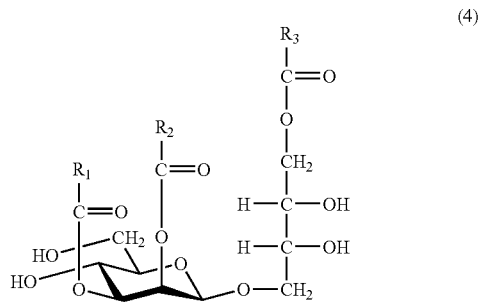

(4)

In chemical formula (4), R1, R2, and R3 independently indicate a carbon hydride group or a carbon hydride group including an oxygen atom. At least one of or both of hydroxyl groups at the 4- and 6-positions of mannose may be replaced with an acetyl group. A carbon hydride group may include only a saturation bond or may include an unsaturation bond. When including an unsaturation bond, the unsaturation bond may include a plurality of double bonds. A carbon chain may be a straight chain or a branched chain. Further, in a case of the carbon hydride group including an oxygen atom, the number and the position of an oxygen atom included in the carbon hydride group are not limited.

In chemical formula (4), it is preferable that R1 and R2 include 6-20 carbon atoms. R1 and R2 make, as fatty series acyl groups (RCO—), ester bonds with hydroxyl groups at 2- and 3-positions of mannose. An acetyl group may make ester bond with other hydroxyl group. It is preferable that R3 has 6-20 carbon atoms. R3 makes, as a fatty series acyl group (RCO—), ester bond with a primary hydroxyl group of erythritol.

A triacyl derivative of MEL has a structure to which fatty acid ester is added and has high hydrophobicity. Therefore, the tryacyl derivative of MEL is excellent as emollient since it is more familiar with various oil components, compared with conventional MEL.

These biosurfactants may be used singularly or two or more of the biosurfactants may be used in combination.

A method for producing the biosurfactant is not particularly limited. Any one of fermentation methods with use of well known biosurfactant-producing-microorganism may be selected. For example, cultural production of MEL can be carried out by culturing *Pseudozyma antarctica* NBRC 10736 through common procedures. Examples of MEL-producing-microorganism include *Candida antarctica, Candida* sp., etc. in addition to the above. It is well known to a person skilled in the art that cultivation of the microorganism easily provides MEL. The biosurfactant-producing-microorganism is not particularly limited and may be suitably selected according to purposes.

A fermentation medium for producing biosurfactants may be a medium with a general composition, made of N source such as yeast essence and peptone, C source such as glucose and fructose, and inorganic salts such as sodium nitrate, dibasic potassium phosphate, and magnesium heptahydrate. Fats and oils such as olive oil, soybean oil, sunflower oil, corn oil, canola oil, and coconut oil, and water-unsoluble bases of carbon hydride such as liquid paraffin and tetradecan may be added singularly to the medium or two or more of them may be added in combination.

Fermentation conditions such as pH and temperature and culture time etc. may be freely set. A culture solution after the fermentation may be used as the biosurfactant of the present invention. Further, the culture solution after the fermentation may be subjected to any operation such as filtering, centrifugal separation, extraction, purification, and sterilization. The obtained essence may be diluted, condensed, and dried.

The fat and oil used as a raw material is preferably plant fat and oil. The plant fat and oil is not particularly limited and may be suitably selected according to necessity. Examples of the plant fat and oil include soybean oil, colza oil, corn oil, peanut oil, cotton seed oil, safflower oil, sesame oil, olive oil, and palm oil. Among them, soybean oil is particularly preferable since it allows increasing production efficiency (production amount, production speed, and yield) of a biosurfactant (MEL in particular). These may be used singularly or two or more of them may be used in combination.

An inorganic nitrogen source is not particularly limited and may be suitably selected according to purposes. Examples of the inorganic nitrogen source include ammonium nitride, urea, sodium nitride, ammonium chloride, and ammonium sulfate.

Recovery and purification of a biosurfactant are not particularly limited and may be suitably selected according to purposes. For example, a culture solution is subjected to centrifugal separation so as to recover oil, and a biosurfactant is recovered by extraction and condensation with use of an organic solvent such as acetic ether.

As an extraction solvent, water, alcohols (lower alcohol such as methanol, absolute ethanol, and ethanol, or polyvalent alcohol such as propylene glycol and 1,3-btyleneglycol), ketones such as acetone, esters such as diethyl ether, dioxane, acetonitrile, and acetic ether, and organic solvents such as xylene, benzene, and chloroform may be used singularly or two or more of them may be used in any combination. Further, various extracts by solvent may be used in combination A method for extracting a biosurfactant is not particularly limited. In general, extraction is carried out in a range from a room temperature to a boiling point of a solvent at a normal pressure. After the extraction, the biosurfactant is filtered or absorbed, decolorized, and purified with use of ion exchange resin so that the biosurfactant is in the shape of a solution, paste, gel, or powder. In many cases, the biosurfactant may be used as it is. If necessary, the biosurfactant may be subjected to a further purification process such as deodorization and decolorization in a range that does not influence the effect of the biosurfactant. Activated carbon column etc. may be used as purification process means for deodorization and decolorization. Normal means generally applied according to an extracted substance may be freely selected. If the biosurfactant is purified with use of a silica gel column according to necessity, it is possible to obtain a biosurfactant with higher purity.

A method for obtaining a triacyl derivative of a biosurfactant is explained below using a method for producing a triacyl derivative of MEL. The triacyl derivative of the bio surfactant used in the present invention is not limited to triacyl MEL.

For example, the triacyl MEL may be obtained by purifying a fraction of the triacyl MEL from a culture solution produced by fermenting a microorganism as described above.

Further, in order to obtain a large amount of the triacyl MEL, MEL is dissolved in an organic solvent, a fatty acid derivative of plant oil etc. is added, and esterification reaction or ester exchange reaction is carried out in the presence of hydrolytic enzyme.

Fatty acid introduced to an erythritol part of MEL may be univalent carboxylic acid of a long-chain carbon hydride. Further, the fatty acid may be saturated fatty acid or unsaturated fatty acid. The unsaturated fatty acid may include a plurality of double bonds. A carbon chain may be straight chain or a branched chain. Further, a fatty acid derivative that is a derivative of fatty acid may be used in the present invention, and a mixture of fatty acid and fatty acid derivative may be used in the present invention. It is preferable that fatty acid or fatty acid derivative introduced into the erythritol part of MEL is derived from oils, higher fatty acid, or synthesized ester.

Examples of the oils include plant oil, animal oil, mineral oil, and hardened oil thereof. Specific examples of the oils include animal/plant oils such as avocado oil, olive oil, sesame oil, camellia oil, evening primrose oil, turtle oil, macadamia nut oil, corn oil, mink oil, colza oil, yolk oil, persic oil, wheat germ oil, sasanqua oil, castor oil, linseed oil, safflower oil, cotton seed oil, perilla oil, soybean oil, peanut oil, tea oil, Japanese torreya seed oil, rice oil, tung oil, jojoba oil, cacao oil, coconut oil, horse oil, palm oil, palm kernel oil, beef tallow, sheep tallow, pig tallow, lanoline, whale wax, beeswax, carnauba wax, Japan wax, candelilla wax, and squalan, and hardened oils thereof; mineral oils such as liquid paraffin and Vaseline, and synthesized triglycerin such as tripalmitin acid glycerin. Preferable examples of the oils include avocado oil, olive oil, sesame oil, camellia oil, evening primrose oil, turtle oil, macadamia nut oil, corn oil, mink oil, colza oil, yolk oil, persic oil, wheat germ oil, sasanqua oil, castor oil, linseed oil, safflower oil, cotton seed oil, perilla oil, soybean oil, peanut oil, tea oil, Japanese torreya seed oil, rice oil. Further preferable examples of the oils include olive oil and soybean oil.

Examples of the higher fatty acid include caproic acid, caprylic acid, capric acid, lauric acid, myristic acid, palmitic acid, oleic acid, linoleic acid, linolenic acid, stearic acid, behenic acid, 12-hydroxy stearic acid, isostearic acid, undecynoic acid, tall acid, eicosapentaenoic acid, and docosahexaenoic acid. Preferable examples of the higher fatty acid include lauric acid, myristic acid, palmitic acid, oleic acid, linoleic acid, linolenic acid, stearic acid, and undecylenic acid. Further preferable examples of the higher fatty acid include oleic acid, linoleic acid, and undecylenic acid.

Examples of the synthesized ester include methyl caproate, methyl caprylate, methyl caprate, methyl laurate, methyl myristate, methyl palmitate, methyl oleate, methyl linoleate, methyl linolenate, methyl stearate, methyl undecynoate, ethyl caproate, ethyl caprylate, ethyl caprate, ethyl laurate, ethyl myristate, ethyl palmitate, ethyl oleate, ethyl linoleate, ethyl linolenate, ethyl stearate, ethyl undecynoate, vinyl caproate, vinyl caprylate, vinyl caprate, vinyl laurate, vinyl myristate, vinyl palmitate, vinyl oleate, vinyl linoleate, vinyl linolenate, vinyl stearate, vinyl undecynoate, cetyl octanoate, octyldodecyl myristate, isopropyl myristate, myristyl myristate, isopropyl palmitate, butyl stearate, hexyl laurate, decyl oleate, dimethyl octanoic acid, cetyl lactate, and myristyl lactate. Preferable examples of the synthesized ester include methyl laurate, methyl myristate, methyl palmitate, methyl oleate, methyl linoleate, methyl linolenate, methyl stearate, and methyl undecylenate. Further preferable examples of the synthesized ester include methyl oleate, methyl linoleate, and methyl undecylenate.

The triacyl MEL can be produced by dissolving MEL in an organic solvent and reacting the MEL. The organic solvent is not particularly limited as long as it can solubilize MEL. The organic solvent only has to solubilize a part of MEL and does not necessarily have to solubilize the whole part of MEL. The organic solvent may be a mixture of a plurality of organic solvents. Specific examples of the organic solvent include methanol, ethanol, propanol, butanol, acetone, propanone, butanone, pentane-2-on, 1,2-ethanediol, 2,3-butanediol, dioxane, acetonitrile, 2-methyl-butane-2-ol, tertiary butanol, 2-methylpropanol, 4-hydroxy-2-methylpentanone, tetrahydrofuran, hexane, DMF, DMSO, pyridine, methyl ethyl ketone. Preferable examples of the organic solvent include acetone, tetrahydrofuran, tertiary butanol, acetonitrile, and dioxane. Further preferable example of the organic solvent is acetone.

Examples of the hydrolytic enzyme include lipase, protease, and esterase. It is preferable to use at least one selected from them. A plurality of the hydrolytic enzymes may be used. Lipase and esterase are preferable, and lipase is further preferable.

Specifically, MEL purified from a culture solution of MEL-producing-microorganism is dissolved in an organic solvent (e.g. acetone) and a commercially available lipase (e.g. novozyme 435 (manufactured by Novozymes)) and plant fat and oil are added to the organic solvent.

In this method, the mixture is stirred for 1-7 days at a reaction temperature of 10-100° C., preferably 20-50° C., and more preferably 25-40° C. Further, molecular sieves may be added to the reaction solution. This method allows MEL added as a material to be a triacyl derivative substantially quantitatively.

Purification of the triacyl MEL may be carried out in accordance with the above purification of MEL.

The biosurfactant obtained as described above may be used as an activator as it is. However, it is preferable to use the biosurfactant in such a manner that the biosurfactant is mixed in cosmetics, quasi-drugs, drugs, and drinks and foods. The concentration with which the biosurfactant is mixed is suitably determined according to the degree of absorption, the degree of operation, the form of a product, the frequency of usage etc., and is not particularly limited. The mixture concentration may be determined in a range that does not impair an operation for activating cells. In general, the mixture concentration is preferably 0.001-50% by mass, more preferably 0.1-20% by mass, and further preferably 1-15% by mass, and particularly preferably 3-10% by mass, with respect to the whole weight of the activator.

Here, the biosurfactant to be mixed in the activator may be used in any form. For example, the biosurfactant may be used as an extract from a culture solution, may be purified and presented as a highly purified product, may be used after being suspended in water, or may be used after being dissolved in an organic solvent such as ethanol.

Although the method of the present invention for producing an activator including a biosurfactant is not particularly limited, Although the method of the present invention for producing an activator including a biosurfactant is not particularly limited, it is preferable to use the biosurfactant in such a manner that the biosurfactant is dissolved in a non-ionic surfactant, lower alcohol, polyvalent alcohol, or natural fat and oil such as olive oil, squalan, and fatty acid, since the biosurfactant is highly hydrophobic.

Examples of the non-ionic surfactant include sorbitan fatty acid esters (e.g. sorbitan monooleate, sorbitan monoisostearate, sorbitan monolaurate, sorbitan monopalmitate, sorbitan monostearate, sorbitan sesquioleate, sorbitan trioleate, penta-2-ethyl hexyl acid diglycerol sorbitan, tetra-2-ethyl hexyl acid diglycerol sorbitan etc.); glycerin polyglycerin fatty acids (e.g. mono cotton seed oil fatty acid glycerin, glycerin monoerucate, glycerin sesquioleate, glycerin monostearate, α, α'-oleic acid pyroglutamic acid glycerin, glycerin monostearate malate etc.); propylene glycol fatty acid esters (e.g. propylene glycol monostearate); hardened castor oil derivative; glycerin alkyl ester etc.

Examples of POE hydrophilic non-ionic surfactant include POE-sorbitan fatty acid esters (e.g. POE-sorbitan monomonooleate, POE-sorbitan monostearate, POE-sorbitan monooleate, POE-sorbitan tetraoleate etc.); POE sorbit fatty acid esters (e.g. POE-sorbit monolaurate, POE-sorbit monooleate, POE-sorbit pentaoleate, POE-sorbit monostearate etc.); POE-glycerin fatty acid esters (e.g. POE-monooleate etc. such as POE-glycerin monostearate, POE-gycerin monoisostearate, POE-glycerin triisostearate); POE-fatty acid esters (e.g. POE-distearate, POE-monodioleate, ethylene glycol distearate etc.); POE-alkylethers (e.g. POE-lauryl ether, POE-oleyl ether, POE-stearyl ether, POE-behenyl ether, POE-2-octyldodecylether, POE-cholestanolether etc.); Pluronic type (such as Pluronic); POE.POP-alkylethers (e.g. POE.POP-cetyl ether, POE.POP-2-decyltetradecylether, POE.POP-monobutylether, POE.POP hydrogenated lanolin, POE.POP-glycerin ether etc.); tetra POE.tetra POP-ethylene diamine condensates (e.g. Tetronic); POE-castor oil hardened castor oil derivative (e.g. POE-castor oil, POE-hardened castor oil, POE-hardened castor oil monoisostearate, POE-hardened castor oil triisostearate, POE-hardened castor oil mono-pyroglutamic acid mono-isostearic acid diester, POE-hardened castor oil maleic acid); POE-beeswax lanolin derivative (e.g. POE-sorbit beeswax etc.); alkanolamide (e.g. palm oil fatty acid diethanolamide, lauric acid monoethernol amide, fatty acid isopropanol amide etc.); POE-propylene glycol fatty acid ester; POE-alkylamine; POE-fatty acid amide; simple sugar fatty acid ester; alkylethoxydimethylamineoxide; trioleyl phosphoric acid etc.

Examples of lower alcohol include ethanol, propanol, isopropanol, isobutylalcohol, t-butylalcohol etc.

Examples of the polyvalent alcohol include bivalent alcohols (such as ethylene glycol, propylene glycol, trimethylene glycol, 1,2-butylene glycol, 1,3-butylene glycol, tetramethylene glycol, 2,3-butyleneglycol, pentamethyleneglycol, 2-butene-1,4-diol, hexylene glycol, octylene glycol); trivalent alcohols (such as glycerin and trimethyloipropane); quadrivalent alcohols (e.g. pentaerythritol etc. such as 1,2,6-hexane triol); pentavalent alcohols (such as xylitol); hexavalent alcohols (such as sorbitol and mannitol); polyvalent alcohol polymers (such as diethylene glycol, dipropylene glycol, triethylene glycol, polypropylene glycol, tetraethylene glycol, diglycerin, polyethylene glycol, triglycerin, tetraglycerin, and polygycerin); bivalent alcohol alkyl ethers (such as ethylene glycol monomethyl ether, ethylene glycol monoethyl ether, ethylene glycol monobutyl ether, ethylene glycol monophenyl ether, ethylene glycol monohexyl ether, ethylene glycol mono 2-methylhexyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether); bivalent alcohol alkyl ethers (such as diethylene glycol monomethyl ether, diethylene glycol monoethyl ether, diethylene glycol monobutylether, diethyleneglycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether and dipropylene glycol butyl ether); bivalent alcohol ether ester (such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate); glycerin monoalkyl ether (such as chimyl alcohol, selachyl alcohol, and batyl alcohol); sugar alcohol (such as sorbitol, maltitol, maltotriose, mannitol, simple sugar, erythritol, glucose, fructose, amylolytic sugar, maltose, xylitose, and amylolytic sugar reducing alcohol); glysolid; tetrahydrofurfuryl alcohol; POE-tetrahydrofurfuryl alcohol; POP-butyl ether; POP.POE-butyl ether; tripolyoxypropylene glycerin ether; POP-glycerin ether; POP-glycerin ether phosphoric acid; POP.POE-pentaerythritol ether, and polyglycerin.

Examples of the oils include animal and plant oils such as avocado oil, olive oil, sesame oil, camellia oil, evening primrose oil, turtle oil, macadamia nut oil, corn oil, mink oil, colza oil, yolk oil, persic oil, wheat germ oil, sasanqua oil, castor oil, linseed oil, safflower oil, cotton seed oil, Perilla oil, soybean oil, peanut oil, tea oil, Japanese torreya seed oil, rice oil, tung oil, jojoba oil, cacao oil, coco oil, horse oil, palm oil, palm kernel oil, beef tallow, lard, lanoline, whale tallow, beeswax, carnauba wax, Japan wax, candellila wax, squalan and hardened oil thereof, mineral oils such as liquid paraffin and Vaseline, and synthesized triglycerin such as tripalmtin acid glycerin.

Examples of the higher fatty acid include lauric acid, myristic acid, palmitic acid, oleic acid, linoleic acid, linolenic acid, stearic acid, behenic acid, 12-hydroxy stearic acid, isostearic acid, undecynoic acid, tall acid, eicosapentaenoic acid, and docosahexaenoic acid. Examples of the higher alcohols include lauric alcohol, cetyl alcohol, stearyl alcohol, behenyl alcohol, myristyl alcohol, oleyl alcohol, cetostearyl alcohol, jojoba alcohol, lanoline alcohol, batyl alcohol, 2-decyltetratececynol, cholesterol, phytosterol, and isostearyl alcohol. Examples of the synthesized ester include cetyl octanoate, octyl dodecyl myristate, isopropyl myristate, myristyl myristate, isopropyl palmitate, butyl stearate, hexyl laurate, decyl oleate, dimethyl octanoic acid, cetyl lactate, and myristyl lactate. Examples of the silicone include chain polysiloxane such as dimethyl polysiloxane and methyl phenyl polysiloxane, cyclic polysiloxane such as decamethylcyclopolysiloxane, and a 3-D matrix structure such as silicone resin.

As described above, it is preferable to embody the activator of the present invention as a composition by mixing a biosurfactant that is an active ingredient with cosmetics, quasi-drugs, drugs, and foods.

In a case of embodying the activator of the present invention in the form of cosmetics, quasi-drugs, and drugs, it is preferable that the activator is for external use. However, since the biosurfactant can be also taken orally, the activator is not limited to external use and may be used for internal use and for foods and drinks.

In a case of using the activator of the present invention as a drug, since it is verified that the biosurfactant has a function for activating human head hair papilla cells, it is possible to use the activator as drugs for promoting hair-growth and preventing progression of loss of hair.

The dosage form of the activator is not limited and may be various forms such as ample, capsule, powder, granulated powder, pill, tablet, a solid agent, a liquid agent, gel, foam, emulsion, cream, ointment, sheet, mousse, and bath agent.

Specifically, examples of the cosmetics, quasi-drugs, and drugs include: drug products for internal and external uses; basic skin care such as skin lotion, emulsion, cream, ointment, lotion, oil, pack; facial wash and skin cleansing agent, hair cosmetics such as shampoo, rinse, hair treatment, hair cream, pomade, hair spray, hair dressing, permanent reagent, hair tonic, hair dye, and hair growth drug and baldness remedy; makeup cosmetics such as foundation, face powder, ceruse, lipstick, blusher, eyeshadow, eyeliner, mascara, eyebrow pencil, and eyelash; make-up cosmetics such as manicure; perfumes; bath agents; tooth pastes; mouth deodorant; mouth wash; hircismus preventing agent/deodorant; sanitary goods; sanitary cottons; and wet tissues.

Specifically, examples of the foods and drinks include: drinks such as soft drink, carbonated drink, energy drink, juice, and lactic acid drink; frozen desserts such as ice cream, ice sherbet, and shaved ice; noodles such as soba, udon, bean-starch vermicelli, crust of potsticker, crust of dumpling, Chinese noodle, and instant noodle; sweets such as lozenge, candy, gum, chocolate, tablet candy, munch, biscuit, jelly, jam, cream, baked cake, and bread; marine products such as crab, salmon, clam, tuna, sardine, shrimp, bonito, mackerel, whale, oyster, saury, squid, ark shell, scallop, ear shell, sea urchin, salmon caviar, and sulculus diversicolor supertexta; marine and animal processed foods such as boiled fish paste, ham, and sausage; dairy products such as processed milk and fermented milk; fats and oils and fat and oil processed foods such as salad oil, frying oil, margarine, mayonnaise, shortening, whip cream, and dressing; seasonings such as source and baste; retort pouch foods such as curry, stew, chicken and egg bowl, rice gruel, zosui, Chinese bowl, pork cutlet bowl, tempura bowl, spicy broiled eel bowl, hashed rice, oden, mapo doufu, beef bowl, meat source, egg soup, omelet rice, potsticker, dumpling, hamburg steak, and meat ball; health and nutriceutical supplements in various forms; functional foods; tablets; capsules; health drinks; and troches.

The activator of the present invention is preferably applicable to human, but may be applied to animals other than human.

The activator of the present invention may include not only the biosurfactant that is an active ingredient but also, if necessary, components and additives that are used in cosmetics, quasi-drugs, drugs, and foods and drinks in a range that does not reduce the effect of the present invention.

Examples of the fats and oils include avocado oil, almond oil, fennel oil, perilla oil, olive oil, orange oil, orange roughy oil, sesame oil, cacao oil, chamomile oil, carrot oil, cucumber oil, beef tallow, beef tallow fatty acid, kukui nut oil, safflower oil, soybean oil, camellia oil, corn oil, colza oil, persic oil, castor oil, cotton seed oil, peanut oil, turtle oil, mink oil, yolk oil, cacao oil, palm oil, palm kernel oil, Japan wax, coco oil, beef tallow, lard, hardened oil, and hardened castor oil.

Examples of tallow include beeswax, carnauba wax, whale wax, lanoline, liquid lanoline, reduced lanoline, hardened lanoline, candellila wax, montan wax, and shellac wax.

Examples of the mineral oil include liquid paraffin, Vaseline, paraffin, ozokerite, ceresin, microcrystalline wax, polyethylene powder, squalene, squalan, and pristane.

Examples of the fatty acids include: natural fatty acids such as lauric acid, myristic acid, palmitic acid, stearic acid, behenic acid, oleic acid, 12-hydroxy stearic acid, undecynoic acid, tall oil, and lanoline fatty acid; and synthesized fatty acids such as isononanoic acid, caproic acid, 2-ethylbutane acid, isopentane acid, 2-methylpentane acid, 2-ethylhexane acid, and isopentane acid.

Examples of the alcohols include: natural alcohols such as ethanol, isopropanol, lauric alcohol, cetanol, stearyl alcohol, oleyl alcohol, lanoline alcohol, cholesterol, and phytosterol; synthesized alcohols such as 2-hexyldecanol, isostearyl alcohol, and 2-octyldodecanol; polyvalent alcohols such as ethylene oxide, ethylene glycol, diethylene glycol, triethylene glycol, ethylene glycol monoethyl ether, ethylene glycol monobutyl ether, diethylene glycol monomethyl ether, diethylene glycol monoethyl ether, polyethylene glycol, propylene oxide, propylene glycol, polypropylene glycol, 1,3-butylene glycol, glycerin, batyl alcohol, pentaerythritol, sorbitol, mannitol, glucose, and simple sugar.

Examples of the esters include isopropyl myristate, isopropyl palmitate, butyl stearate, hexyl laurate, myristyl myristate, oleyl oleate, decyl oleate, octyl dodecyl myristate, hexyl decile dimethyloctanoate, cetyl lactate, myristyl lactate, diethyl phthalate, dibutyl phthalate, lanoline acetate, ethyleneglycol monostearate, propylene glycol monostearate, propylene glycol dioleate.

Examples of the metal soap include aluminum stearate, magnesium stearate, zinc stearate, calcium stearate, zinc palmitate, magnesium myristate, zinc laurate, and zinc undecylenate.

Examples of gummy and water-soluble macromolecular compositions include gum Arabic, benzoin gum, dammar gum, guaiac, Irish moth, karaya gum, tragacanth gum, carob gum, quince seed, agar, casein, dextrin, gelatin, pectin, starch, carrageenan, carboxy alkyl chitin, chitosan, hydroxy alkyl chitin, low molecular chitosan, chitosan salt, sulfated chitin, phosphorylated chitin, alginic acid and salt thereof, hyaluronic acid and salt thereof, chondroitin sulfate, heparin, ethylcellulose, methylcellulose, carboxy methylcellulose, carboxy ethylcellulose, carboxyethyl cellulose sodium, hydroxyethylcellulose, hydroxypropylcellulose, nitrocellulose, crystalline cellulose, polyvinyl alcohol, polyvinyl methyl ether, polyvinyl pyrrolidone, polyvinyl methacrylate, polyacrylic acid salt, polyalkylene oxide such as polyethylene oxide and polypropylene oxide and crosslinking polymer thereof, carboxy vinyl polymer, polyethylene imine.

Examples of the surfactants include anionic surfactant (such as carboxylate, sulfonate, sulfate ester salt, and phosphoric ester salt), cationic surfactant (such as amine salt and quaternary ammonium salt), ampholytic surfactant (carboxylic acid ampholytic surfactant, sulfate ester ampholytic surfactant, sulfonic acid ampholytic surfactant, and phosphate ester ampholytic surfactant), non-ionic surfactant (such as ether non-ionic surfactant, ether ester non-ionic surfactant, ester non-ionic surfactant, block polymer non-ionic surfactant, and nitrogen-containing non-ionic surfactant), and other surfactant (such as natural surfactant, derivative of protein hydrolysate, macromolecular surfactant, surfactant including titan and silicon, and carbon fluoride surfactant.

Examples of vitamins include retinol, retinal (vitamin A1), dehydroretinal (vitamin A2), carotin, and lycopene (protovitamine A) in vitamin A group; thiamine hydrochloride, thiamine hydro sulfate (vitamin B1), riboflavin (vitamin B2), pyridoxine (vitamin B6), cyanocobalamin (vitamin B12), folic acids, nicotinic acids, pantothenic acids, biotins, choline, inositols in vitamin B group; ascorbic acid and derivative thereof in vitamin C group; ergocalciferol (vitamin D2), cholecalciferol (vitamin D3), and dihydrotachysterol in vitamin D group; tocopherol and derivative thereof and ubiquinone in vitamin E group; phytonadione (vitamin K1), menaquinone (vitamin K2), menadione (vitamin K3), and menadiol (vitamin K4) in vitamin K group.

Examples of amino acids include valine, leucine, isoleucine, threonine, methionine, phenylalanine, tryptophan, lysine, glycine, alanine, asparagine, glutamine, serin, cysteine, cystine, tylosine, proline, hydroxyproline, asparaginic acid, glutamic acid, hydroxylysine, arginine, ornithine, histidine, hydrosulfates thereof, phosphates thereof, nitrates thereof, citrates thereof, and amino acid derivatives such as pyrrolidone carboxylic acid.

Examples of whitening agents include ascorbic acid and derivative thereof, sulfur, hydrolysate of placenta, ellagic acid and derivative thereof, kojic acid and derivative thereof, glucosamine and derivative thereof, arbutin and derivative thereof, hydroxycinnamic acid and derivative thereof, glutathione, arnica essence, essence of root of scultellaria baicalensis, essence of root bark of morus ihou, essence of root of bupleurum scorzonerifolium, essence of root of saposhnikovia seseloides, culture of mycelium of Ganoderma lucidum and extract thereof, essence of linden, essence of peach leaves, essence of fruit of rosa multiflora, essence of root of sophora flavescens, essence of Sanguisorba officinalis, essence of angelica acutiloba, essence of seed of Job's tears, essence of persimmon leaves, essence of pieplant, essence of root bark of peony, essence of hamamelis, essence of marronnier, essence of hypericum erectum, essence of oil-soluble licorice.

Examples of moisture retention agents include hyaluronic acid, polyglutamine acid, serin, glycine, threonine, alanine, collagen, hydrolyzed collagen, hydronectin, fibronectin, keratin, elastin, royal jelly, chondroitin heparin sulfate, glycerophospholipid, glyceroglycolipid, sphingophospholipid, sphingoglycolipid, linoleic acid and esters thereof, eicosapentaenoic acid and esters thereof, pectine, bifidobacteria fermentation product, lactic acid fermentation product, yeast extract, culture of mycelium of Ganoderma lucidum and extract thereof, wheat germ oil, avocado oil, rice oil, jojoba oil, soybean phospholipid, γ-oryzanol, essence of Althaea officinalis, essence of seed of Job's tears, essence of root of Rehmannia glutinosa, essence of fruit of jujube, essence of seaweed, essence of aloe arborescens, essence of burdock, essence of rosemary, essence of arnica, and wheat bran.

Examples of the hair growth drug include pentadecanic acid glyceride, essence of coleus, essence of gentiana lutea, essence of conifer cone, essence of royal jelly, essence of sasa veitchii, t-flavanone, 6-benzyl amino purine, essence of swertia japonica, carpronium chloride, minoxidil, finasteride, adenosine, nicotinic acid amide, essence of mulberry roots, essence of rehmannia glutinosa, and 5-aminol evulinic acid.

Examples of extracts and essences of animals, plants, and galenicals include Uncaria gambir, Angelica keiskei, acerola, Althaea, Arnica montana, avocado, Hydrangea macrophylla var. thunbergii, Aloe, Aloe vera, nettle, Ginkgo, fennel, turmeric, Asarum sieboldii, ume, Quercus salicina, Arctostaphylos uva-ursi, Rosa multiflora, Rabdosia japonica, membranous milk-vetch, Scutellaria baicalensis (dried root of Scutellaria baicalensis), Prunus jamasakura, Phellodendron amurense, Coptis japonica, Panax ginseng, Hypericum erectrum, Lamium album var. barbatum, Watercress, orange, Polygala tenuifolia, Prunella vulgaris subsp. asiatica, Polygonum multiflorum, Pagoda Tree, mugwort, Zedoary, Kudzu, Valeriana fauriei, chamomile, Trichosanthes kirilowii var. japonica, Artemisia capillaris Thunb, licorice, Tussilago farfara, Bramble, kiwifruit, balloon flower, Chrysanthemum, Catalpa ovata, Rutaceae plant fruit (unripened fruit of Citrus aurantium or Citrus natsudaidai), Citrus tachibana, cucumber, Aralia cordata, Angelica pubescens, apricot, Chinese Wolfberry, Sophora flavescens, Camphor tree, Sasa veitchii, grapefruit, Cinnamon, Schizonepeta tenuifolia, Senna obtusifolia, Ipomoea purpurea, morning glory, Safflower, Sumac, Comfrey, Copaiba, gardenia, gentiana, Magnolia obovata (bark of Magnolia obovata), achyranthes bidentata (root thereof), tetradium ruticarpum (fruit thereof), burdock, schisandra chinensis (fruit thereof), rice, rice bran, wheat, bupleurum schorzonerifolium (root thereof), saffron, Saponaria officinalis, hawthorn, Japanese pepper, salvia, panax pseudoginseng, Chinese mushroom, rehmannia glutinosa (root thereof), Quisqualis indica, lithospermum erythrorhizon (root thereof), perilla, persimmon (sepal of fruit thereof), peony, plantago asiatica (seed thereof, whole parts thereof), ginger, iris, glossy privet (fruit thereof), filipendula multijuga, white birch, Japanese honeysuckle (bud thereof), hedera helix, achillea millefolium, elder, adzuki bean, Japanese red elder, malva sylvestris, cnidium officinale makino, Japanese green gentian, mulberry (root bark thereof, leaves thereof), jujube, soybean, aralia elata, panax japonicus, anemarrhena asphodeloides (bulb thereof), sanguisorba officinalis (root thereof), houttuynia cordata, Caterpillar fungus, pepper, Chinese lantern plant, thyme, green tea, black tea, clove, citrus unshiu (exocarp thereof), camellia, contella asiatica, pepper, angelica acutiloba (root thereof), calendula officinalis, citrus aurantium (exocarp of fruit thereof), sanguisorba officinalis (root thereof), corn (style of gynoecium thereof), eucommia ulmoides (bark thereof, leaves thereof), tomato, nandina domestica (fruit thereof), garlic, barley (malt), Pictamnus albus (bark of root of Pictamnus albus), Ophiopogon japonicus (Ophiopogon japonicus tuber), parsley, batata, mint, hamamelis, rose, leaves of loquat, Poria cocos, grape or leaves thereof, dishcloth gourd, tilia miqueliana, peony (root bark thereof), hop, Rosa rugosa, pine needle, marronnier, rosemary, soapberry, melissa, melilot, Japanese quince, bean sprout, peach (inner core of seed thereof, leaves thereof), Belamcanda chinensis, betel palm tree, leonurus sibiricus, cornflower, saxifraga stolonifera (leaves thereof), myrica rubura (bark thereof), alnus firma, Job's tears (seed of Job's tears), Artemisia Mongolia, artemisia montana, lavender, apple fruit, varnished conk, lemon fruit, Forsythia suspensa (fruit thereof), Chinese milk vetch, geranium thunbergii (geranium), scopolia japonica (bulb and root thereof), crest of chicken, placental extract of cattle and human, extract or resolvent of stomach, duodenum, or intestines of pig and cattle, water-soluble collagen, water-soluble collagen derivative, hydrolysis of collagen, elastin, hydrolysis of elastin, water-soluble elastin derivative, silk protein, resolvent of silk protein, and decomposition product of bovine blood cell protein.

Examples of the microorganism culture metabolites include yeast essence, zinc-containing yeast essence, germanium-containing yeast essence, selenium-containing yeast essence, magnesium-containing yeast essence, fermented rice essence, euglena extract, lactic fermentation product of skimmed milk.

Examples of the α-hydroxy acid include glycol acid, citric acid, malic acid, tartaric acid, and lactic acid.

Examples of the inorganic colorings include silicic acid anhydride, magnesium silicate, talc, kaolin, bentonite, mica, titanium mica, bismuth oxychloride, zirconium oxide, magnesium oxide, zinc oxide, titanium oxide, calcium carbonate, magnesium carbonate, iron oxide yellow, colcothar, iron oxide black, ultramarine, chromium oxide, chromium hydroxide, carbon black, and calamine.

Examples of the ultraviolet ray absorber include p-amino benzolin acid derivative, salicylic acid derivative, anthranilic acid derivative, coumarin derivative, amino acid compound, benzotriazole derivative, tetrazole derivative, imidazoline derivative, pyrimidine derivative, dioxane derivative, camphor derivative, furan derivative, pyrone derivative, nuclear acid derivative, allantoin derivative, nicotinic acid derivative, vitamin B6 derivative, oxybenzone, benzophenone, guaiazulene, shikonin, baicalin, baicalein, and berberine.

Examples of the astringent include laconic acid, tartaric acid, succinic acid, citric acid, allantoin, zinc chloride, zinc sulfate, zinc oxide, calamine, p-phenol zinc sulfonate, aluminum calium sulfonate, resorcin, iron chloride, and tannic acid.

Examples of the antioxidant include ascorbic acid and salt thereof, ester stearate, tocopherol and ester derivative thereof, nordihydroguaceretenic acid, buthylhydroxy toluene (BHT), buthylhydroxy anisole (BHA), parahydroxy anisole, propyl gallate, sesamol, sesamolin, and gossypol.

Examples of the anti-inflammatory agent include ichthammol, indomethacin, kaolin, salicylic acid, sodium salicylate, methyl salicylate, acetylsalicylic acid, diphyenhydramine chloride, d- or dl-camphor, hydrocortisone, guaiazulene, chamazulene, chlorpheniramine maleate, glycyrrhizin acid and salt thereof, glycyrrhetic acid and salt thereof.

Examples of the fungicide and disinfectant include acrinol, sulfur, benzalkonium chloride, benzethonium chloride, methylrosaniline chloride, cresol, calcium gluconate, chlorhexidine gluconate, sulfamine, mercurochrome, lactoferrin and hydrolysates thereof.

Examples of the hair care agent include selenium disulfide, alkyl isoquinolinium bromide liquid, zinc pyrithione, biphenamine, thianthol, kasutari tincture, ginger tincture, pepper tincture, quinine hydrochloride, strong ammonia water, potassium bromate, sodium bromate, and thioglycolic acid.

Examples of the aroma chemical include: natural animal aroma chemical such as musk, civet, castoreum, and ambergris; plant aroma chemicals such as anis essential oil, angelica essential oil, ylang-ylang essential oil, iris essential oil, fennel essential oil, orange essential oil, cananga essential oil, caraway essential oil, cardamom essential oil, guaiac wood essential oil, cumin essential oil, lindera essential oil, cassia essential oil, cinnamon essential oil, geranium essential oil, copaiba balsam essential oil, coriander essential oil, perrilla essential oil, cedar wood essential oil, citronella essential oil, jasmine essential oil, ginger grass essential oil, cedar essential oil, spearmint essential oil, peppermint essential oil, Ferula gummosa essential oil, tuberose essential oil, clove essential oil, orange flower essential oil, wintergreen essential oil, tolu balsam essential oil, Patchouli essential oil, rose essential oil, palmarosa oil, Japanese cypress essential oil, Japanese cypress essential oil, sandal wood oil, petitgrain essential oil, bay essential oil, vetiver essential oil, bergamot essential oil, balsam of Peru essential oil, bois de rose essential oil, camphor tree essential oil, mandarin essential oil, eucalyptus essential oil, lime essential oil, lavender essential oil, linaloe essential oil, lemon grass essential oil, lemon essential oil, rosemary essential oil, and Japanese mint essential oil; and other synthetic aroma chemicals.

Examples of the coloring and coloring matter include red cabbage coloring, red rice coloring, Rubia argyi coloring, annatto coloring, sepia coloring, turmeric coloring, sophora coloring, krill coloring, persimmon coloring, caramel, gold, silver, gardenia coloring, corn coloring, onion coloring, tamarind coloring, spirulina coloring, buckwheat coloring, cherry coloring, layer coloring, hibiscus coloring, grape juice coloring, marigold coloring, purple potato coloring, purple yam coloring, lac coloring, and rutin.

Examples of the sweetening include sugar, *Hydrangea macrophylla*, fructose, arabinose, galactose, xylose, mannose, maltlose, honey, glucose, miraculin, and monellin.

Examples of the nutritional additive include calcinated shell calcium, cyanocolabamin, yeast, wheat germ, soybean embryo, yolk powder, hemicellulose, and heme iron.

Other examples of materials that may be included in the activator of the present invention include hormones, chelating agent, pH adjuster, chelating agent, antiseptic, fungicide, refrigerant, stabilizer, emulsifier, animal/plant proteins and decomposition products thereof, animal/plant polysaccharides and decomposition products thereof, animal/plant glycoproteins and decomposition products thereof, blood flow promoting agent, anti-inflammatory agent and anti-allergy agent, cell activator, keratolytic agent, wound healing drug, foam boosting agent, thickener, agent for oral use, deodorant, bittering agent, seasoning, and oxygen.

<2. Anti-Aging Method>

Usage of the bio surfactant that is an active ingredient of the activator of the present invention allows providing an anti-aging method. That is, the present invention encompasses an anti-aging method with use of the bio surfactant.

The anti-aging method of the present invention includes the step (i) of causing the biosurfactant to touch an animal. The biosurfactant is preferably at least one selected from a group consisting of mannosyl erythritol lipid (MEL), mannosyl mannitol lipid (MML), a triacyl derivative of mannosyl erythritol lipid (MEL), and a triacyl derivative of mannosyl mannitol lipid (MML).

The animal is not particularly limited as long as an anti-aging effect of the biosurfactant can be expected. A preferable example of the animal is a mammal. A further preferable example of the animal is a human.

"Causing the biosurfactant to touch an animal" indicates causing the biosurfactant to touch a range where an external agent can be applied, such as skin and mucous membrane of the animal.

The anti-aging method of the present invention further includes the step (ii) of activating cells with use of the biosurfactant. Activating cells with use of the biosurfactant having a cell-activating function allows yielding an anti-aging effect such as preventing and improving wrinkles, sags, and hardening of skin so as to maintain resilient, youthful, and healthy skin.

Embodiment 2

The following explains another embodiment of the present invention.

<1. Mannosyl erythritol lipid (MEL)>

In order to aid understanding of MEL of the present invention, the following outlines conventional MEL.

The conventional MEL is produced through cultivation of a MEL-producing microorganism. A representative example of the chemical structure of the conventional MEL is shown by general formula (5) below. The chemical structure includes 4-O-β-D-mannopyranosyl-meso-erythritol as a basic structure thereof.

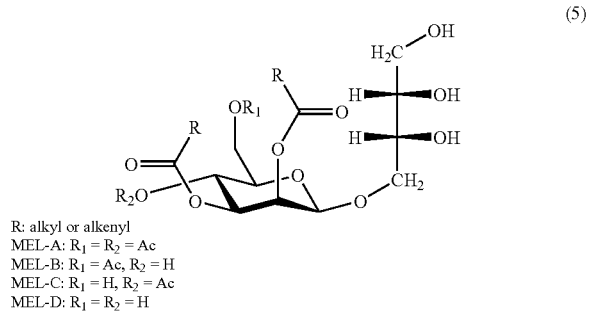

R: alkyl or alkenyl
MEL-A: $R_1 = R_2 = Ac$
MEL-B: $R_1 = Ac, R_2 = H$
MEL-C: $R_1 = H, R_2 = Ac$
MEL-D: $R_1 = R_2 = H$ In the general formula (5), a substituent R is a hydro carbon group (alkyl group or alkenyl group). Four kinds of the conventional MEL are known according to whether an acetyl group at 4- and 6-positions of mannose exists or not. The four kinds include MEL-A, MEL-B, MEL-C, and MEL-D.

MEL-A is designed such that each of substituents R1 and R2 is an acetyl group in the general formula (5). MEL-B is designed such that the substituent R1 is an acetyl group and the substituent R2 is hydrogen in the general formula (5). MEL-C is designed such that the substituent R1 is hydrogen and the substituent R2 is an acetyl group in the general formula (5). MEL-D is designed such that each of the substituents R1 and R2 is hydrogen in the general formula (5).

The number of carbons in the substituent R of the MEL-A, MEL-B, MEL-C, and MEL-D varies according to the number of carbons in fatty acid constituting triglyceride in fats and oils included in an MEL-producing medium and the degree of assimilation of fatty acid by MEL producing microorganism in use. In a case where the triglyceride includes an unsaturated fatty acid residue, when the MEL producing microorganism do not assimilate a double-bonding section of the unsaturated fatty acid, it is possible for MEL to include the unsaturated fatty acid residue as the substituent R. As is evident from the above, each resulting MEL is generally a mixture of compounds having different fatty acid residues of the substituents R.

On the other hand, MEL of the present invention has a structure represented by the general formula (1) and is an optical isomer in which erythritol is introduced in a direction opposite to that of the conventional MEL. In the general formula (1), the substituents $R^1$ may be the same or different from each other and are fatty series acyl groups having 4-24 carbon atoms, and the substituents $R^2$ may be the same or different from each other and represent hydrogen or acetyl groups. Further, the substituent $R^3$ represents a fatty series acyl group having 2-24 carbon atoms. Note that the present invention excludes MEL where both of the substituents $R^1$ are fatty series acyl groups having 12 carbon atoms, both of the substituents $R^2$ are acetyl groups, and the substituent $R^3$ is hydrogen. This is indented to exclude the MEL disclosed in Non-patent Document 8 from the present invention, and is not indented for any other purpose. This exclusion is not a limitative matter that unduly limits the scope of the present invention.

Further, the substituent $R^1$ in the general formula (1) may be a fatty series acyl group or an unsaturated fatty series acyl group, and is not particularly limited. When the substituent $R^1$ includes an unsaturated bond, the substituent $R^1$ may include a plurality of double bonds. The carbon chain may be a straight chain or a branched chain. Further, in a case of hydrocarbon group containing an oxygen atom, the number and the position of the contained oxygen atom are not limited.

Further, it is preferable that one of the substituents $R^2$ is an acetyl group and the other of the substituents $R^2$ is hydrogen. That is, it is preferable that the MEL of the present invention is a 1-O-MEL and is MEL-B or MEL-C. In particular, it is further preferable that the MEL of the present invention has hydrogen at 4-position and an acetyl group at 6-position, i.e. MEL-B.

For example, compared with MEL-A (having two acetyl groups), MEL-B or MEL-C (having one acetyl group) has higher polarity and different in its self-assembly behavior in water. Consequently, formed liquid crystals have different phases. In MEL-A, a sponge phase ($L_3$ phase) etc. is formed in a wide concentration region, whereas in MEL-B or MEL-C, a lamella phase ($L_a$ phase) is likely to be formed. The lamella phase is very similar to a keratin layer of skin, making the MEL have high skin-permeability and effective as a skin-care material. Further, in MEL-B, a bimolecular film is likely to form a capsuled vesicle (liposome), which allows the capsule to include a drug therein. Therefore, it is expected that MEL-B is easily applicable to liposome cosmetics and drugs (see Non-patent Documents 9 and 10).

The MEL synthesized in Non-patent Document 8 is of A type, and includes two fatty acids each being C12. In contrast thereto, the present invention allows producing MEL-B or MEL-C, and widely varying the length of a fatty acid chain. This allows providing MEL having an ability to form more different liquid crystals.

Note that the synthesizing method described in Non-patent Document 8 is limited to a method for synthesizing MEL-A. In order to synthesize MEL-B and MEL-C, it is necessary to use different protective groups and to repeat different step. Therefore, the MEL of the present invention could not have been synthesized based on Non-patent Document 8.

In the general formula (1), it is preferable that the substituent $R^3$ is a fatty series acyl group having 2-24 carbon atoms. When both of the substituents $R^1$ and $R^3$ are fatty series acyl groups, the MEL is triacyl MEL that has properties different from those of diacyl MEL.

Specifically, a triacyl derivative is a surfactant having lower HLB (hydrophilic-hydrophobic balance) and higher lipophilicity than a conventional diacyl derivative. Therefore, the triacyl derivative is used for purposes different from those of the diacyl derivative. For example, the triacyl derivative can be used for W/O emulsion, a dispersing agent etc. Further, as with the above case, the synthesizing method described in Non-patent Document 8 is limited to a method for synthesizing a diacyl derivative of MEL-A, and synthesizing a triacryl derivative would require entirely different synthesizing route (different protective groups and different multi-stage reactions). Therefore, the MEL of the present invention could not have been produced based on Non-patent Document 8.

The chemical structure of the MEL of the present invention can be obtained in the form of a mixture made of compounds that are different according to the number of carbons in a fatty series acyl group that is the substituent $R^1$ in the general formula (1) or to whether a double bond exists or not. the compounds can be made a single MEL compound by purifying with use of a preparative HPLC.

As with the conventional MEL, the MEL of the present invention has high surface-activity, and unlike the conventional MEL, the MEL of the present invention has new physiological activity and self-assembling property, and therefore can be used as a surfactant or various catalysts for fine chemicals. Further, the MEL is very significant since it has high biodegradability and highly safe. That is, the MEL is a bio-surfactant that has high biodegradability, low toxicity, and is environment-friendly.

It is reported that the conventional MEL has various bioactive functions. For example, it is reported that MEL has the following functions: when MEL is caused to act on strain of human acute promyelocytic leukemia cellulous HL 60, MEL shows a promyelocytic cell differentiation inducing function for differentiating ganulocytes; when MEL is caused to act on PC 12 cells derived from rat adrenal medulla melanocytoma, MEL shows neural system cell differentiation inducing function etc. for elongating neuritis; and for the first time among glycolipids produced by a microorganism, MEL can induce apoptosis of melanoma cells (X. Zhao et. al, Cancer Research, 59, 482-486 (1999)), and hence MEL has a function for preventing proliferation of cancer cells. In consideration of the bioactive functions of the conventional MEL, it is expected that the MEL of the present invention also has various bioactive functions and is applicable to drugs such as an anticancer agent and a new cosmetic material.

Further, as explained in later-mentioned Examples, the MEL of the present invention is significantly different in liquid crystal forming ability from the conventional MEL due to the difference in chilarity of molecules. Specifically, the MEL of the present invention has an ability to produce a lamella phase in a concentration area greatly wider than that of the conventional MEL. Therefore, the MEL of the present invention is a biosurfactant that is extremely excellent in the ability to form liquid crystals.

Evaluation of the ability to form liquid crystals can be made by a conventional and publicly known method. An example of the method for easily comparing the ability to form liquid crystals is a water invading method. In this method, MEL is applied on a slide glass and distilled water is dropped beside the applied area, and a liquid crystal phase formed at an interface by dropping of the distilled water is observed by a microscope. Thus, behavior of liquid crystal formation can be searched. With the method, it is possible to easily compare the conventional MEL with the MEL optical isomer of the present invention in terms of their abilities to form liquid crystals.

<2. Method for Producing MEL>

The method for producing the MFL of the present invention is characterized by usage of a microorganism capable of producing 1-O-MEL. Specifically, it is a method including the step of culturing a microorganism that belongs to *Pseudozyma* genus and is capable of producing mannosyl erythritol lipid, so as to produce mannosyl erythritol lipid having the structure represented by the general formula (1). In the descriptions explaining the method for producing the MEL of the present invention, in the general formula (1), the substituents $R^1$ may be the same or different from each other and are fatty acid acryl groups having 4-24 carbons, the substituents $R^2$ may be the same or different from each other and represent hydrogen or acetyl groups, and the substituent $R^3$ represents hydrogen or fatty series acyl group having 2-24 atoms.

<2-1. Microorganism in Use>

Examples of the microorganism useable in the method of the present invention for producing MEL is not particularly limited as long as the microorganism belongs to *Pseudozyma* genus and produces the MEL optical isomer represented by the general formula (1).

Examples of the microorganism that produces the MEL represented by the general formula (1) include microorganism that belong to *Pseudozyma tsukubaensis*, *Pseudozyma crassa* etc. In particular, the microorganism belonging to *Pseudozyma tsukubaensis* is preferable. The microorganism belonging to *Pseudozyma tsukubaensis* has high productivity at 25-30° C. for example. In particular, *Pseudozyma tsukubaensis* JCM 10324 strain has the highest productivity at a culture temperature of 30° C.

<2-2. Culture Medium in Use and Culture Method>

The culture medium may be a culture medium generally used for general microorganisms and yeasts, and is not particularly limited. A culture medium used for yeasts is particularly preferable. An example of such culture medium is a YPD culture medium (10 g of yeast extract, 20 g of polypepton, and 100 g of glucose). It is known that preferable culture temperature for *Pseudozyma tsukubaensis* JCM 10324 strain ranges from 27-33° C. This is because *Pseudozyma tsukubaensis* JCM 10324 strain has significantly high productivity of MEL at the temperature.

The composition of a culture medium suitable for producing MEL with use of a microorganism usable for the method of producing the MEL of the present invention, in particular *Pseudozyma tsukubaensis* JCM 10324 strain, is as follows.

Yeast essence: preferably 0.1-2 g/L, and particularly preferably 1 g/L

Sodium nitrate: preferably 0.1-1 g/L, and particularly preferably 0.3 g/L

Potassium dihydrogen phosphate: preferably 0.1-1 g/L, and particularly preferably 0.3 g/L Magnesium sulfate: preferably 0.1-1 g/L, and particularly preferably 0.3 g/L Fats and oils: preferably 40 g/L or more, and particularly preferably 80 g/L Further, when culturing the microorganism, it is preferable that a carbon source is added to a culture medium. The carbon source includes at least one of, or a mixture of, fats and oils, fatty acid, fatty acid derivative (fatty acid esters such as fatty acid triglyceride) and synthesized ester. Other conditions of the carbon source are not particularly limited and may be determined suitably in accordance with a technical standard at the time of usage of the present invention.

The "fats and oils" may be plant oils, animal oils, mineral oils, and hardened oils thereof. Specific examples of the fats and oils include: animal/plant oils such as avocado oil, olive oil, sesame oil, camellia oil, evening primrose oil, turtle oil, macadamia nut oil, corn oil, mink oil, colza oil, yolk oil, persic oil, peanut oil, safflower oil, wheat germ oil, sasanqua oil, castor oil, linseed oil, safflower oil, cotton seed oil, perilla oil, soybean oil, arachis oil, tea oil, Japanese torreya seed oil, rice oil, tung oil, jojoba oil, cacao oil, coconut oil, horse oil, palm oil, palm kernel oil, beef tallow, sheep tallow, lard, lanoline, whale wax, beeswax, carnauba wax, Japan wax, candellila wax, and squalan and hardened oils thereof; mineral oils such as liquid paraffin and Vaseline; and synthesized triglycerin such as glycerin tripalmitate. Preferable examples of the fats and oils include avocado oil, olive oil, sesame oil, camellia oil, evening primrose oil, turtle oil, macadamian nut oil, corn oil, mink oil, colza oil, yolk oil, persic oil, wheat germ oil, sasanqua oil, castor oil, linseed oil, safflower oil, cotton seed oil, perilla oil, soybean oil, arachis oil, tea oil, Japanese torreya seed oil, rice oil. Further preferable examples of the fats and oils include olive oil and soybean oil.

"Fatty acid" or "fatty acid derivative" preferably derives from higher fatty acid. Examples of the fatty acid and the fatty acid derivative include capronic acid, caprylic acid, capric acid, lauric acid, myristic acid, palmitic acid, oleic acid, linoeic acid, linolenic acid, stearic acid, behenic acid, 12-hydroxy stearic acid, isostearic acid, undecynoic acid, tall acid, eicosapentaenoic acid, and docosahexaenoic acid. Preferable examples of the fatty acid and the fatty acid derivative include lauric acid, myristic acid, palmitic acid, oleic acid, linoeic acid, linolenic acid, stearic acid, and undecynoic acid. Further preferable examples of the fatty acid and the fatty acid derivative include oleic acid, linoeic acid, and undecynoic acid.

Examples of the synthesized ester include methyl caproate, methyl caprylate, methyl caprate, methyl laurate, methyl myristate, methyl palmitate, methyl oleate, methyl linoleate, methyl linolenate, methyl stearate, methyl undecynoate, ethyl caproate, ethyl caprylate, ethyl caprate, ethyl laurate, ethyl myristate, ethyl palmitate, ethyl oleate, ethyl linoleate, ethyl linolenate, ethyl stearate, ethyl undecynoate, vinyl caproate, vinyl caprylate, vinyl caprate, vinyl laurate, vinyl myristate, vinyl palmitate, vinyl oleate, vinyl linoleate, vinyl linolenate, vinyl stearate, vinyl undecynoate, cetyl octanoate, octyldodecyl myristate, isopropyl myristate, myristyl myristate, isopropyl palmitate, butyl stearate, hexyl laurate, decyl oleate, dimethyl octanoic acid, cetyl lactate, and myristyl lactate. Preferable examples of the synthesized ester include methyl laurate, methyl myristate, methyl palmitate, methyl oleate, methyl linoleate, methyl linolenate, methyl stearate, and methyl undecylenate. Further preferable examples of the synthesized ester include methyl oleate, methyl linoleate, and methyl undecylenate.

These may be used singularly or two or more of them may be used suitably in combination.

Specific steps of the method for producing MEL of the present invention are not particularly limited and may be determined suitably according to purposes. For example, it is preferable that the steps are scaled up in the order of seed culture, main culture, and culture for producing MEL. The following shows culture media and culture conditions for these cultures.

a) Seed culture; 1 platinum loop is inoculated to a test tube containing 5 mL of a liquid culture medium including 40 g/L of glucose, 1 g/L of yeast essence, 0.3 g/L of sodium nitrate, 0.3 g/L of potassium dihydrogen phosphate, and 0.3 g/L of magnesium sulfate, and the liquid culture medium is subjected to shaking culture at 30° C. for 1 day.

b) Main culture; the culture solution of a) is inoculated to a Sakaguchi flask containing 100 mL of a liquid culture medium including a predetermined amount of fat and oil such as plant fat and oil, 1 g/L of yeast essence, 0.3 g/L of sodium nitrate, 0.3 g/L of potassium dihydrogen phosphate, and 0.3 g/L of magnesium sulfate, and the culture solution is cultured at 30° C. for 2 days.

c) Culture for producing mannosyl erythritol lipid; the culture solution is inoculated to a jar fermenter containing 1.4 L of a liquid culture medium including a predetermined amount of fat and oil such as plant fat and oil, 1 g/L of yeast essence, 0.3 g/L of sodium nitrate, 0.3 g/L of potassium dihydrogen phosphate, and 0.3 g/L of magnesium sulfate, and cultured at 30° C. with a stirring speed of 800 rpm. In the culture, it is preferable that plant fat and oil is flowed into the culture vessel in the course of the culture so that the concentration of the fat and oil in the culture medium is kept at 20-200 g/L.

<2-3. Method for Collecting MEL>

A method for collecting MEL may be a conventional and publicly known method and is not particularly limited. For example, after the culture, a lipid component is extracted with use of ethyl acetate whose volume is not less than the volume of the lipid component and not more than four times of the lipid component, and then ethyl acetate is removed with use of an evaporator so as to collect the lipid component and glycolipid component. Thereafter, the lipid component is dissolved in chloroform whose volume is equal to the volume of the lipid component, and is treated with silica gel chromatography so that chloroform, chloroform:acetone (80:20), chloroform:acetone (70:30), chloroform:acetone (60:40), chloroform:acetone (50:50), chloroform:acetone (30:70), and acetone are eluted in this order. Each solution is charged to a thin layer chromatography (TLC) plate, and is developed with a ratio of chloroform:methanol: ammonia water=65: 15:2 (volume ratio). After the development, whether glycolipid exists or not is confirmed with use of an anthrone sulfuric acid reagent. An eluate containing glycolipid is gathered, a solvent is removed, and thus the glycolipid component can be obtained.

<2-4. Structural Determination of MEL>

Structural determination of the MEL obtained by the method for producing the MEL may be performed by a conventional and publicly known method and is not particularly limited. For example, the following explains structural determination of MEL with reference to a structural determination method of MEL obtained with use of *Pseudozyma tsukubaensis* JCM 10324 strain.

The isolated glycolipid component can be determined as glycolipid component since the glycolipid component shows blue-green in response to an anthrone sulfuric acid reagent on the TLC plate. Whether the glycolipid is MEL or not can be easily confirmed by subjecting the glycolipid to $^1$H, $^{13}$C, and two-dimensional NMR analyses and comparing the obtained spectrum with the spectrum of conventional MEL (MEL-A, MEL-B, MEL-C, and MEL-D) (represented by the general formula (4)) whose structure has been already known.

With use of 1) NMR analysis of sugar skeleton and 2) measurement of optical rotation that are mentioned below, it is easily confirmed that the MEL of the present invention is an optical isomer of conventional MEL.

1) NMR Analysis of Sugar Skeleton

In $^1$H-NMR spectrum measured in chloroform-d, proton of a sugar chain of MEL is detected near 3.3-5.6 ppm. In particular, proton at a mannose 1'-position (reducing terminal) that contributes to glycoside bind and proton at erythritol 4-position are detected near 4.7 ppm and near 4.0 ppm, respectively. However, it is reported by D. Crich et al. that when directions in binding of erythritol are different, the peaks due to the above protons shift (see Non-patent Document 8). Therefore, it is confirmed whether the MEL of the present invention shows spectrum patterns shifted only by the above peaks with respect to the conventional MEL.

Further, a sugar chain (mannosyl erythritol; which may hereinafter be abbreviated as ME) obtained by saponifying the resulting MEL with use of alkali (NaOCH$_3$) is subjected to NMR analysis. By comparing a sugar chain of the resulting MEL with a sugar chain of the conventional MEL in terms of their NMR spectra, it is possible to confirm that the structure of a sugar chain of the MEL of the present invention shows a spectrum pattern different from that of the conventional MEL (4-O-β-D-mannnopyranosyl-meso-erythritol structure).

2) Measurement of Optical Rotation

By measuring optical rotation of MEL or ME, it is possible to compare chirality of molecules of the conventional MEL with chirality of molecules of the MEL of the present invention (see Non-patent Document 8). 1-O-(4',6'-di-O-acetyl-2', 3'-di-O-dodecyl-β-D-mannno pyranosyl)-D-erythritol that is reported by D. Crich et al. and that has the same sugar skeleton as the MEL of the present invention has specific optical rotation HD=−25.9° (c=1.5). Comparison of the MEL of the present invention with the conventional MEL with reference to the specific optical rotation shows the difference in three-dimensional structures between the MEL of the present invention and the conventional MEL.

The above method allows confirming that the MEL of the present invention is different from the conventional MEL in terms of three-dimensional structures of sugar skeletons.

As described above, with the method for producing MEL of the present invention, it is possible to selectively produce MEL whose chirality is different from that of the conventional MEL and which has not been reported to be produced by a microorganism. As explained above, difference in chirality of molecules has great influence on physiological activity and a self-assembling body forming function. Consequently, although the MEL of the present invention has the same surface activity as that of the conventional MEL, the MEL of the present invention is different from the conventional MEL in terms of other properties. Therefore, comparison of the MEL of the present invention with the conventional MEL in terms of their physical properties shows important factors for evaluation of functions of MEL. Consequently, storage of data concerning a structure-physical property relationship such as physiological activity greatly contributes to development of usage of biosurfactants in various fields such as drugs, foods, and cosmetics.

The MEL of the present invention appears to be theoretically synthesized by a chemical synthesis method. However, the chemical synthesis of the MEL of the present invention would require an extremely special synthesis technique and multiple stages of complicated protection/deprotection reactions. Further, it is extremely difficult to completely control chirality, and therefore it is extremely difficult to chemically synthesize the MEL of the present invention in reality. In contrast thereto, the production method of the present invention that uses a microorganism includes an elaborate biosynthesis step and therefore provides a method for producing MEL with only one step while maintaining a special structure in which position/three-dimensional structure is completely controlled. Therefore, the method can be very effective.

It is additionally remarked that MEL whose mannosyl erythritol skeleton in a molecular structure is 1-O-β-D-manno pyranosyl meso-erythritol, which is described in Embodiment 2, may be combined with the invention described in Embodiment 1.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

EXAMPLES

The following explains the present invention further specifically with reference to Examples. Note that the following is merely an example and the present invention is not limited to this.

Example 1

Cell-Activating Function of MEL on Normal Human Skin Fibroblasts

Normal human skin fibroblasts were cultured by a common procedure with use of a normal human skin fibroblast total kit (CA106K05, manufactured by Cell Applications. Inc. USA, imported and sold by TOYOBO CO., LTD).

Normal human skin fibroblasts were inoculated to a microplate having 48 holes, so that $2.0 \times 10^4$ cells were inoculated to each well. An inoculation medium was a Dulbecco's Modified Eagle's Medium (DMEM) to which 10% of fetal calf serum was added. The cells were cultured at 37° C. with 5vol % of carbon dioxide concentration for 24 hours, and then the cells were put in a test medium to which MEL-A with final concentration of 1 ng/ml-0.01 mg/ml was added, and the cells were further cultured for 48 hours. MEL-A used in the present Example was obtained by culturing *Pseudozyma antarctica* NBRC 10736 in a medium to which soybean oil was added (3% soybean oil, 0.02% $MgSO4.H_2O$, 0.02% KH2PO4, 0.1% yeast extract).

MEL-A was dissolved in ethanol and then diluted stepwise by ethanol, and was added to each medium so that final concentration of ethanol was 0.5% in each medium. A solvent control was an ethanol group (final concentration was 0.5%). Further, in order to confirm that cytotoxic substance prevents cell proliferation, an SDS-added group (final concentration was 0.1%) was provided. Further, the cells were put in a medium containing 100 μg/mL of 3-(4,5-dimethyl-2-thiazolyl)-2,5-diphenyl tetrazolium bromide (MTT) and was cultured for 3 hours, and formazan produced by ring-opening of a tetrazolium ring was extracted with use of 2-propanol, and absorption of light of 550 nm was measured by a microplate reader. At the same time, absorption of light of 650 nm was measured as turbidity, and cell-activating function was evaluated based on the difference between the two measurement values.

The result of the evaluation is shown in FIG. 1 by relative values with the cell-activating function of an ethanol group (solvent control group) being 100.

As is evident from FIG. 1, the MEL-A-added group showed a higher cell-activating function than the ethanol group with respect to normal human skin fibroblasts at each concentration. In particular, in a case of adding MEL-A whose final concentration was 1 ng/ml, a significant cell-activating function that was higher by 65% or more than the ethanol group was observed. This result shows that MEL has an excellent cell-activating function, which suggests that application of MEL to skin yields an extremely excellent anti-aging effect, effectively improving wrinkles, sags etc. of skin due to aging, exposure to ultra violet ray etc.

Example 2

Cell-Activating Function of MEL on Human Head Hair Papilla Cells (1) How to Culture Human Head Hair Papilla Cells Human hair papilla cells were cultured through a normal procedure with use of human head hair papilla cells (THPC-001) total kit (HDPC total kit: THPCK-001, manufactured by Cell Applications. Inc. USA, imported and sold by TOYOBO CO., LTD). Human head hair papilla cells are widely used for evaluating medicinal benefits of a hair growth drug (see Japanese Unexamined Patent Publications No. 2006-83084, No. 2003-81793, and No. 2000-159640).

Specifically, 10 mL of a PCGM medium for suspending thawed cells were dispensed in a 15 mL centrifugal tube and cooled by ice. A vial containing the thawed human head hair papilla cells (THPC-001) was rapidly melted in a thermostatic chamber at 37° C. The PCGM medium was gradually dropped by approximately 1 mL into the vial and DMSO was diluted, and then the total amount was moved to the centrifugal tube containing the PCGM medium and were suspended. Floating cells were subjected to centrifugal separation by a cooling slow centrifuge at 4° C. with 1000 rpm for 5 minutes. Supernatant was sucked while taking care not to suck precipitated cells, and the supernatant was suspended again in a 1 mL PCGM medium. The total amount was put in a T-75 flask coated with a collagen liquid, and the T-75 flask was put in an incubator under a humidified condition with 5vol % of carbon dioxide concentration at 37° C., and the total amount was subjected to a static culture. One day later, the medium was replaced. Thereafter, the medium was replaced every two days and a subculture was carried out.

The PCGM medium was obtained by adding 2.5 mL of 100-fold dilution of bovine pituitary extract (BPE), 2.5 mL of 100-fold dilution of fetal calf serum (FCS), 1.25 mL of 200-fold dilution of insulin transferrin triiodothyronine solution (ITT), and 1.25 mL of 200-fold dilution of thyroprotein solution (Cyp) to 250 mL of a PCGM basal medium containing 1% of FBS.

(2) Evaluation of Human Head Hair Papilla Cell-Activating Function

Human head hair papilla cells were inoculated to a microplate having 48 holes, so that $2.0 \times 10^4$ cells were inoculated to each well. An inoculation medium was a Dulbecco's Modified Eagle's Medium (DMEM) to which 10% of fetal calf serum was added. The cells were cultured for 24 hours, and then put in a test medium to which MEL-A with final concentration of 1 ng/ml-0.01 mg/ml was added, and the cells were further cultured for 48 hours. MEL-A used in the present Example was obtained by culturing *Pseudozyma antarctica* NBRC 10736 in a medium to which soybean oil was added (3% soybean oil, 0.02% MgSO4.H2O, 0.02% KH2PO4, 0.1% yeast extract).

MEL-A was dissolved in ethanol and then diluted stepwise by ethanol, and was added to each medium so that final concentration of ethanol was 0.5% in each medium. A solvent control was an ethanol group (final concentration was 0.5%). Further, the cells were put in a medium containing 100 μg/mL of 3-(4,5-dimethyl-2-thiazolyl)-2,5-diphenyl tetrazolium bromide (MTT) and was cultured for 3 hours, and formazan produced by ring-opening of a tetrazolium ring was extracted with use of 2-propanol, and absorption of light of 550 nm was measured by a microplate reader. At the same time, absorption of light of 650 nm was measured as turbidity, and cell-activating function was evaluated based on the difference between the two measurement values.

Figure 2:
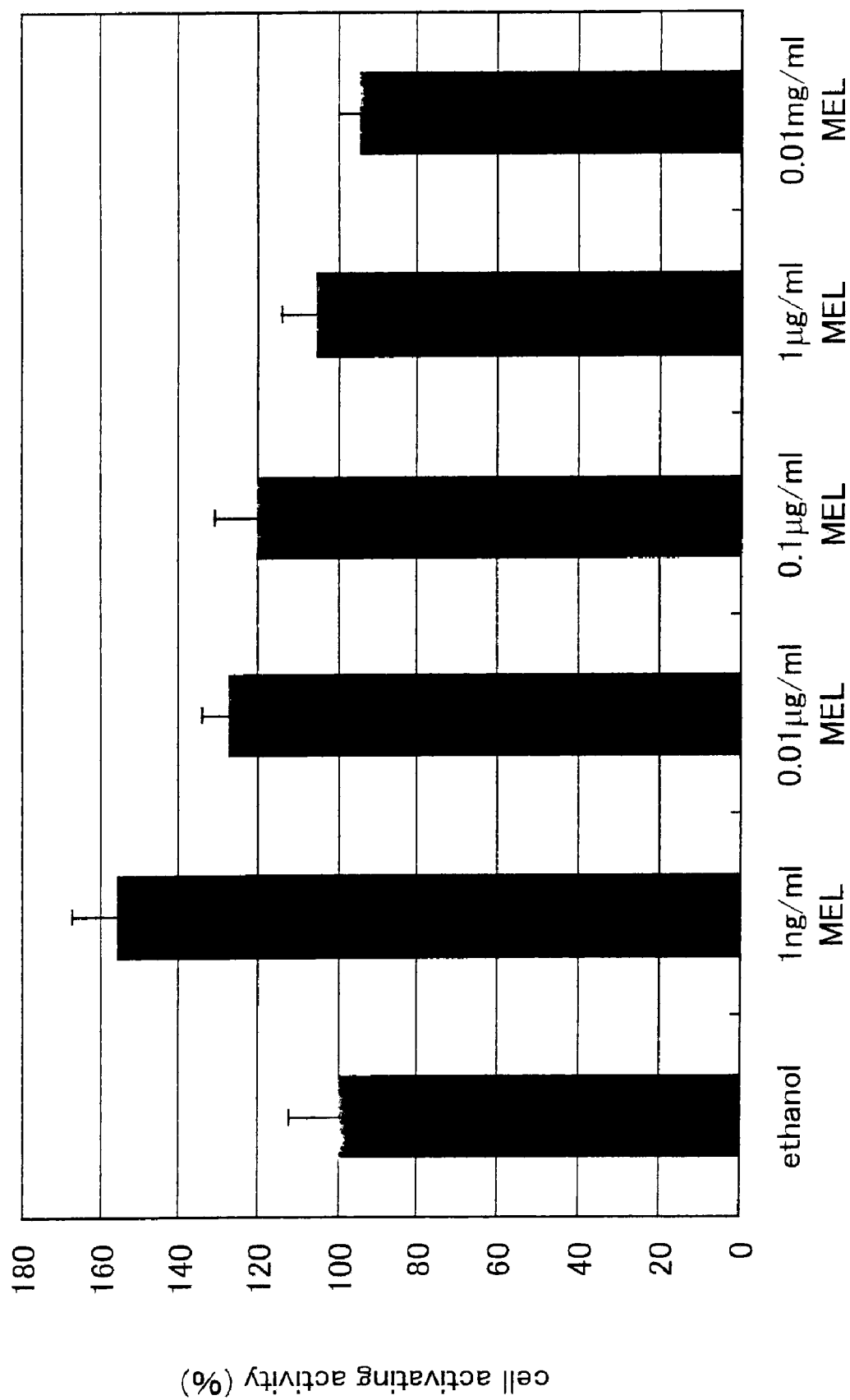
FIG. 2 is a graph showing the result of examining a cell-activating function of MEL (MEL-A produced from soybean oil) on human head hair papilla cells.

The result of the evaluation is shown in FIG. 2 by relative values with the cell-activating function of an ethanol group (solvent control group) being 100.

As is evident from FIG. 2, the MEL-A-added group showed a higher cell-activating function than the ethanol group with respect to human head hair papilla cells in a range of 1 ng/ml-1 μg/ml. In particular, in a case of adding MEL-A whose final concentration was 1 ng/ml, a significant cell-activating function that was higher by 50% or more than the ethanol group was observed. This result suggests that application of MEL to head skin yields an extremely excellent effect of activating hair papilla cells, which yields a hair-growing effect.

Example 3

Cell-Activating Function of Triacyl MEL on Normal Human Skin Fibroblasts

Triacyl MEL was OL-MEL (SB) that was obtained by adding oleic acid to a hydroxyl group of an erythritol portion of MEL-A cultured in a soybean oil-added medium (3% soybean oil, 0.02% $MgSO_4.H_2O$, 0.02% $KH_2PO_4$, 0.1% yeast extract).

Normal human skin fibroblasts were cultured by a common procedure with use of a normal human skin fibroblast total kit (CA106K05, manufactured by Cell Applications. Inc. USA, imported and sold by TOYOBO CO., LTD).

Normal human skin fibroblasts were inoculated to a microplate having 48 holes, so that $2.0 \times 10^4$ cells were inoculated to each well. An inoculation medium was a Dulbecco's Modified Eagle's Medium (DMEM) to which 10% of fetal calf serum was added. The cells were cultured at 37° C. with 5vol % of carbon dioxide concentration for 24 hours, and then the cells were put in a test medium to which the triacyl MEL (OL-MEL (SB)) with final concentration of 0.01 ng/ml-0.01 mg/ml was added, and the cells were further cultured for 48 hours. The triacyl MEL was dissolved in ethanol and then diluted stepwise by ethanol, and was added to each medium so that final concentration of ethanol was 0.5% in each medium. A solvent control was an ethanol group (final concentration was 0.5%). Further, in order to confirm that cytotoxic substance prevents cell proliferation, an SDS-added group (final concentration was 0.1%) was provided. Further, the cells were put in a medium containing 100 μg/mL of 3-(4,5-dimethyl-2-thiazolyl)-2,5-diphenyl tetrazolium bromide (MTT) and was cultured for 3 hours, and formazan produced by ring-opening of a tetrazolium ring was extracted with use of 2-propanol, and absorption of light of 550 nm was measured by a microplate reader. At the same time, absorption of light of 650 nm was measured as turbidity, and cell-activating function was evaluated based on the difference between the two measurement values.

Figure 3:
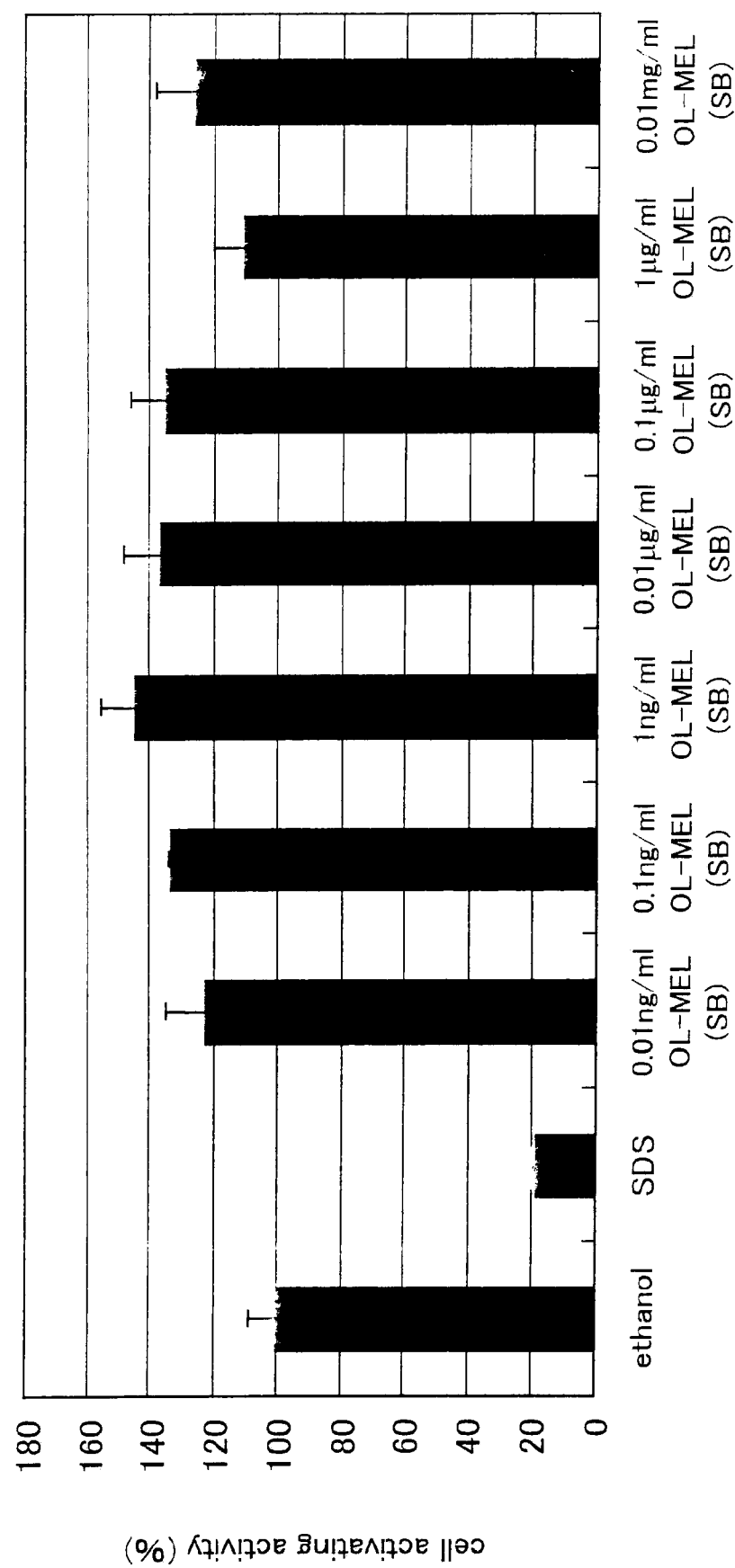
FIG. 3 is a graph showing the result of examining a cell-activating function of triacyl MEL (triacyl MEL-A obtained by adding oleinic acid to a hydroxide group of an erythritol part of MEL-A produced from soybean oil) on normal human skin fibroblasts.

The result of the evaluation is shown in FIG. 3 by relative values with the cell-activating function of an ethanol group (solvent control group) being 100.

As is evident from FIG. 3, the triacyl MEL-added group showed a higher cell-activating function than the ethanol group with respect to normal human skin fibroblast cells at each concentration. In particular, in a case of adding the triacyl MEL whose final concentration was 1 ng/ml, a significant cell-activating and anti-aging function that was higher by approximately 50% than the ethanol group was observed. This result shows that the triacyl MEL has an excellent cell-activating function as with MEL-A, which suggests that application of the triacyl MEL to skin yields an extremely excellent anti-aging effect, effectively improving wrinkles, sags etc. of skin due to aging, exposure to ultra violet ray etc.

Examples 4-6 as described below show examples of prescriptions of various dosage forms of a cell-activator of the present invention.

Example 4

Essence

Essence having the following composition was produced by a common procedure.

| (Composition) | (Weight %) |
| --- | --- |
| Sorbit | 4.0 |
| Dipropylene glycol | 6.0 |
| Polyethylene glycol 1500 | 5.0 |
| POE (20) oleyl alcohol ether | 0.5 |
| Simple sugar fatty acid ester | 0.2 |
| Methyl cellulose | 0.2 |
| MEL | 1.0 |
| Purified water | amount that makes the whole amount of essence 100 |

Example 5

Emulsion

An emulsion having the following composition was produced by a common procedure.

| (Composition) | (Weight %) |
|---|---|
| Glyceryl ether | 1.5 |
| Simple sugar fatty acid ester | 1.5 |
| Sorbitan monostearate | 1.0 |
| Squalan | 7.5 |
| Dipropylene glycol | 5.0 |
| MEL | 1.0 |
| Purified water | amount that makes the whole amount of emulsion 100 |

Example 6

Cream

Cream having the following composition was produced through a common procedure.

| (Composition) | (Weight %) |
|---|---|
| Propylene glycol | 6.0 |
| Dibutyl phthalate | 19.0 |
| Stearic acid | 5.0 |
| Glycerin monostearate | 5.0 |
| Sorbitan monostearate | 12.0 |
| Polyethylene sorbitan monostearate | 38.0 |
| Edetate sodium | 0.03 |
| MEL | 1.0 |
| Purified water | amount that makes the whole amount of cream 100 |

Example 7

Sensory Evaluation

Examples 4-6 were subjected to sensory evaluation. Comparative examples that did not include biosurfactants were also subjected to the same sensory evaluation. In the sensory evaluation, a group consisting of six evaluators of 26-48 years old, conscious about aging symptoms such as wrinkles, used the Examples and the Comparative Examples twice a day continuously for 3 months, and the evaluators were questionnaired as to the conditions of their skins after 3 months.

The result of the sensory evaluation is shown in Table 1 in which the number of evaluators in individual items is shown. 70% or more evaluators answered that the Examples made their skins more resilient and more improved their wrinkles than the Comparative examples that did not include biosurfactants did. This shows that the Examples have a significant effect of improving aging symptoms on skins.

TABLE 1

| | | Examples (with biosurfactant) | | | Comparative Examples (without biosurfactant) | | |
|---|---|---|---|---|---|---|---|
| | | 4 | 5 | 6 | 4 | 5 | 6 |
| Resiliency of skin | Improved | 2 | 4 | 3 | 0 | 0 | 0 |
| | Rather improved | 2 | 0 | 1 | 0 | 0 | 0 |
| | No change | 2 | 2 | 2 | 6 | 5 | 4 |
| | Worsened | 0 | 0 | 0 | 0 | 1 | 2 |
| Improvement | Improved | 3 | 2 | 2 | 0 | 0 | 0 |
| | Rather improved | 1 | 1 | 2 | 1 | 0 | 1 |
| | No change | 2 | 3 | 2 | 5 | 6 | 4 |
| | worsened | 0 | 0 | 0 | 0 | 0 | 1 |

Example 8

Culture of *Pseudozyma tsukubaensis* JCM 10324 Strain a) *Pseudozyma tsukubaensis* JCM 10324 strain preserved in a preservation medium (3 g/L of malt essence, 3 g/L of yeast essence, 5 g/L of peptone, 10 g/L of glucose, and 30 g/L of agar) was inoculated by one platinum loop into a test tube containing 2 mL of a liquid medium including 20 g/L of glucose, 1 g/L of yeast essence, 0.3 g/L of sodium nitrate, 0.3 g/L of potassium dihydrogen phosphate, and 0.3 g/L of magnesium sulfate, and the *Pseudozyma tsukubaensis* JCM 10324 strain was subjected to shaking culture at 30° C. Then, b) 1 mL of a resulting bacterial culture solution was inoculated into a Sakaguchi flask containing 20 mL of a liquid culture including a predetermined amount of soybean oil, 1 g/L of yeast essence, 0.3 g/L of sodium nitrate, 0.3 g/L of potassium dihydrogen phosphate, and 0.3 g/L of magnesium sulfate, and was subjected to shaking culture at 30° C.

The bacterial culture solution obtained in the cultures a) and b) was subjected to the following test.

Example 9

Confirmation of Ability of *Pseudozyma tsukubaensis* JCM 10324 Strain to Produce Glycolipid The culture a) was carried out for 1 day and then the culture b) was carried out for 7 days, and a culture solution was sampled. Using the culture solution, production of a biosurfactant by *Pseudozyma tsukubaensis* JCM 10324 strain was confirmed by thin layer chromatography. A developing solvent included chloroform, methanol, 7N ammonia water in the ratio of 65:15:2, respectively. An indicator was an anthrone sulfuric acid reagent that colors glycolipid in blue-green. Standard MEL was a purified authentic sample obtained by culturing *Pseudozyma antarctica* KM-34 (FERMP-20730) strain in a soybean oil-added medium and removing impurities such as raw material fats and oils etc. MEL-A, MEL-B, MEL-C, and MEL-D indicate compounds represented by the general formula (5) in the standard MEL.

Figure 4:
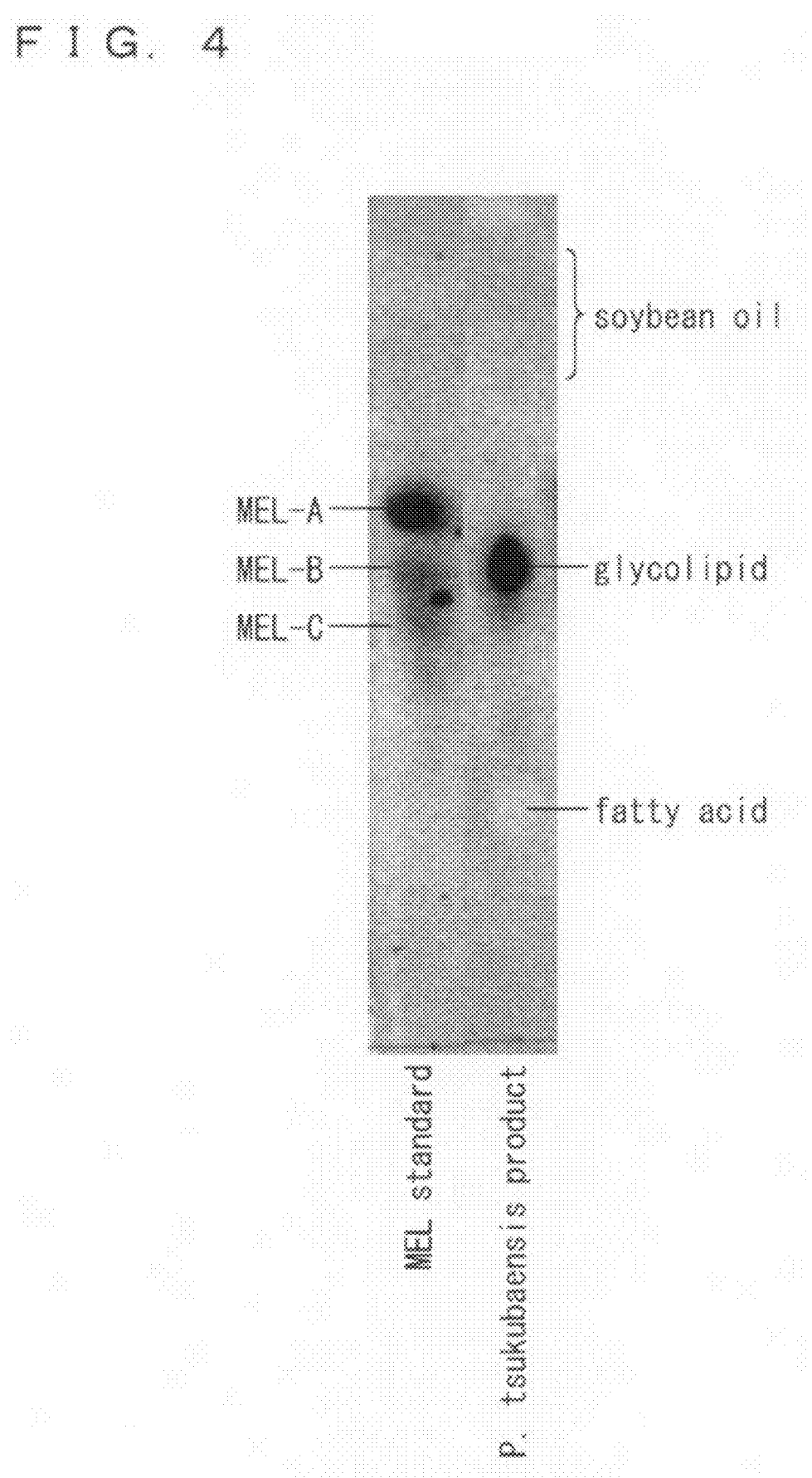
FIG. 4 is a drawing showing the result of thin layer chromatography on a culture of *Pseudozyma tsukubaensis* JCM 10324 strain.

The result is shown in FIG. 4. FIG. 4 shows that *Pseudozyma tsukubaensis* JCM 10324 strain produced glycolipid that seems to be MEL-B.

Example 10

Production of MEL in a Medium for Producing MEL

Using *Pseudozyma tsukubaensis* JCM 10324 strain, the culture a) was carried out for 1 day, and then the culture b) was carried out for 7 days. Thereafter, the culture solution was sampled, a component that was soluble in ethyl acetate was purified from the culture solution, and then the produced MEL was detected by high performance liquid chromatography. In Comparative Example, a culture solution obtained by culturing *Pseudozyma antarctica* KM-34 (FERMP-20730) strain with use of soybean oil as a carbon source was detected by high performance liquid chromatography.

Figure 5:
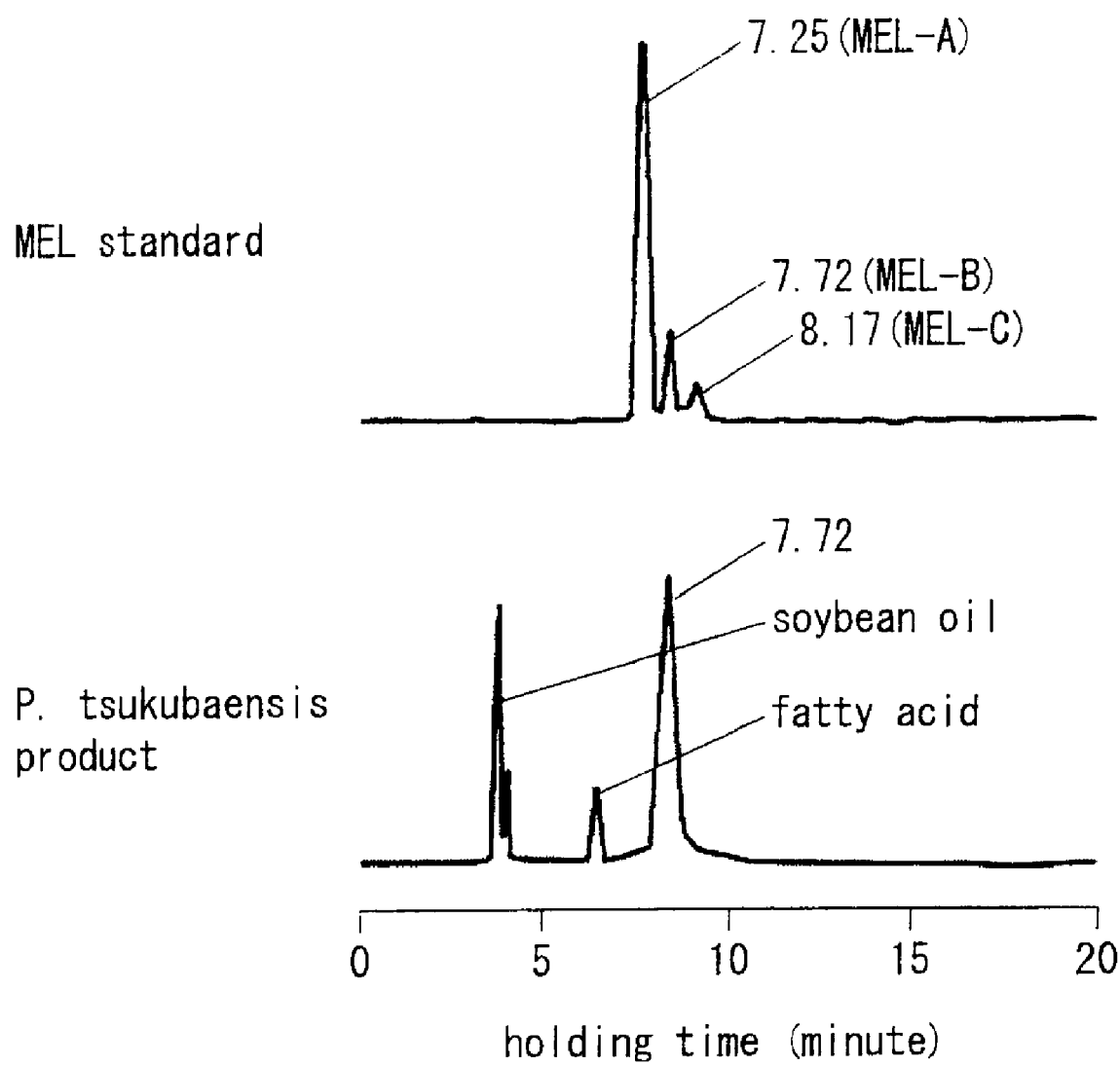
FIG. 5 is a drawing showing the result of analyzing high-performance liquid chromatography on a culture of *Pseudozyma tsukubaensis* JCM 10324 strain.

The results of the detections are shown in FIG. 5. FIG. 5 shows that by culturing *Pseudozyma tsukubaensis* JCM 10324 strain, it is possible to obtain glycolipid whose peak was seen at the same retention time as MEL-B.

Example 11

Culture of *Pseudozyma crassa* CBS 9959 Strain and Confirmation of Ability to Produce MEL

*Pseudozyma crassa* CBS 9959 strain was subjected to the method in Example 8 except that the temperature was 25° C. The culture a) was carried for 1 day and then the culture b) was carried for 7 days, and a culture solution was sampled. Using the culture solution, production of a biosurfactant by *Pseudozyma crassa* CBS 9959 strain was confirmed by thin layer chromatography, as in the method in Example 9.

Figure 6:
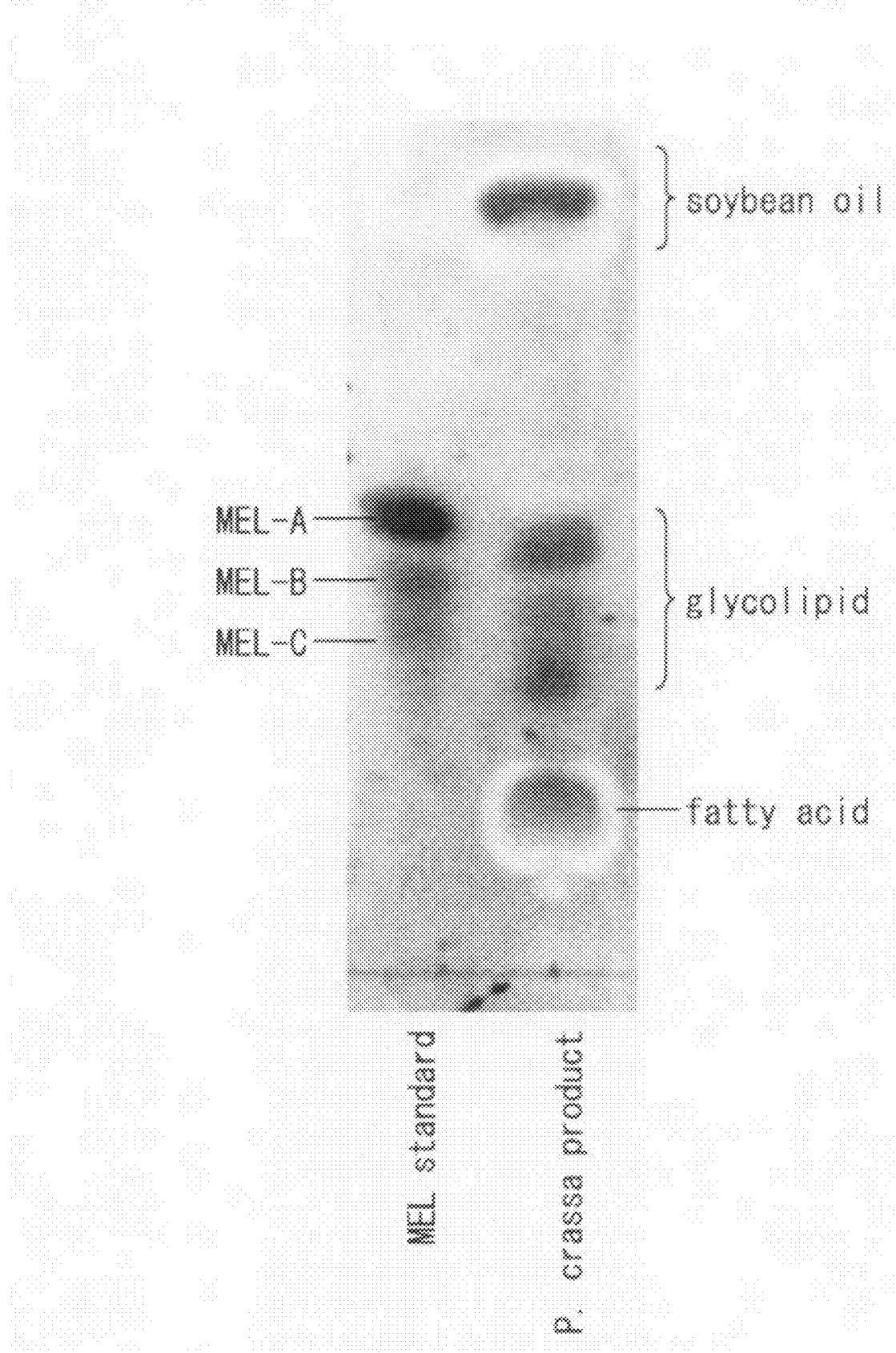
FIG. 6 is a drawing showing the result of thin layer chromatography on a culture of *Pseudozyma crassa* CBS 9959 strain.

The result of the confirmation is shown in FIG. 6. FIG. 6 shows that *Pseudozyma crassa* CBS 9959 strain produced glycolipid whose Rf value was a little lower than already known MEL (MEL-A, MEL-B, and MEL-C).

Example 12

Structure Elucidation of MEL Produced by *Pseudozyma tsukubaensis* JCM 10324 Strain Initially, NMR analysis of a sugar skeleton was carried out. Glycolipid obtained in Example 9 was isolated and purified by a known separation method using silica gel column chromatography, and $^1$H-NMR analysis was carried out using deuterated chloroform (CDCl$_3$). As a comparative object, conventional MEL-B that was produced by culturing *Pseudozyma antarctica* KM-34 (FERMP-20730) strain and then isolated and purified was measured in the same manner.

The results are shown in FIG. 7. FIG. 7 shows that glycolipid produced by *Pseudozyma tsukubaensis* JCM 10324 strain was MEL-B. Further, it was confirmed that 1'-position of mannose (H-1' in the drawing) was shifted toward a lower magnetic field, i.e. from 4.73 ppm to 4.76 ppm, and proton at 4-position of erythritol that were largely separated into two parts (3.8 ppm, 4.0 ppm) were greatly shifted to be one (3.9 ppm). This result is completely in accordance with the descriptions of Non-patent Document 8 reported by D. Crich et al., which demonstrates that erythritol derived from MEL produced by *Pseudozyma tsukubaensis* JCM 10324 strain was bonded in a manner reverse to the manner of conventional MEL.

Further, in order to make more detailed comparison of the structure of sugar skeleton, ester bond in the MEL was subjected to alkali hydrolysis with use of sodium methoxide in methanol. A product obtained after the reaction was precipitated again in ethyl acetate to collect, and was subjected to recrystallizing operation in a 90% ethanol aqueous solution. Thus, crystals of sugar chains (manno erythritol; ME) was obtained.

Sugar chains were collected from conventional MEL in the similar manner, and the obtained ME was subjected to $^1$H, $^{13}$C-, and various two-dimensional NMR analyses using heavy water (D$_2$O) as a solvent.

Consequently, as illustrated in FIG. 8, only proton at 4-position of erythritol shifted its peak (H-4a: 3.85 ppm→3.89 ppm, H-4b: 4.12 ppm→4.0 ppm). M. Kurz et al. carried out detailed structure elucidation of 4-O-β-mannnopyranosyl-D-erythritol (described as 1-O-βmannnopyranosyl-L-erythritol in the Document) that was prepared from usuchi lipid having the same structure as that of conventional MEL (J. Antibiot., 56, 91-101 (2003)), and described that chemical shift of proton at 4-position of conventional ME was such that H-4a was 3.76 ppm and H-4b was 4.09 ppm. The known document describes that in the conventional ME (and MEL), proton at 4-position of erythritol was largely separated into two parts. This shows that MEL of the present invention is new MEL that is an optical isomer of conventional MEL and that includes as a sugar skeleton structure 1-O-β-mannnopyranosyl-D-erythritol where erythritol was bonded in a reverse manner.

Subsequently, optical rotation of the ME was measured. ME was synthesized through alkali hydrolysis in the above manner from MEL obtained by culturing *Pseudozyma antarctica* KM-34 (FERMP-20730) strain and *Pseudozyma tsukubaensis* JCM 10324 strain, and dissolved in distilled water to prepare a 1% aqueous solution. Optical rotation of each aqueous solution was measured with use of a polarimeter (digital polarimeter DIP 370 type manufactured by JASCO Corporation) so as to obtain specific optical rotation of each ME.

Consequently, specific optical rotation of ME derived from *Pseudozyma antarctica* KM-34 (FERMP-20730) was $[\alpha]_D=-35.2°$ and specific optical rotation of ME derived from *Pseudozyma tsukubaensis* JCM 10324 strain was $[\alpha]_D=-39.6°$. This shows that chiralities of sugar skeletons (ME) of MEL produced from respective strains are different, which demonstrates that MEL produced by *Pseudozyma tsukubaensis* JCM 10324 strain is an optical isomer whose 3-dimensional structure of sugar skeleton is different from that of conventional MEL.

Further, ME derived from *Pseudozyma antarctica* KM-34 (FERMP-20730) was obtained as white powder through the above collecting operation and had a melting point of 156.9° C., whereas ME derived from *Pseudozyma tsukubaensis* JCM 10324 strain was obtained as a transparent, colorless, and oily compound, and a melting point of the ME could not be measured. This shows that the two ME have different molecular 3-dimensional structures and have different crystallinity.

It was confirmed from the above result that MEL produced by *Pseudozyma tsukubaensis* JCM 10324 strain obtained in Example 9 is MEL-B and is 1-(6'-acetyl-2',3'-di-O-alka(ke)noyl-β-D-mannnopyranosyl-)meso-erythritol that is an optical isomer of conventional MEL-B.

Example 13

Structure Elucidation of MEL Produced by *Pseudozyma crassa* CBS 9959 Strain

Glycolipids produced by *Pseudozyma crassa* CBS 9959 strain obtained in Example 11 were isolated and purified as in Example 12. Three kinds of glycolipids were subjected to $^1$H-NMR analysis and were compared with conventional MEL-A, MEL-B, and MEL-C.

Figure 9:
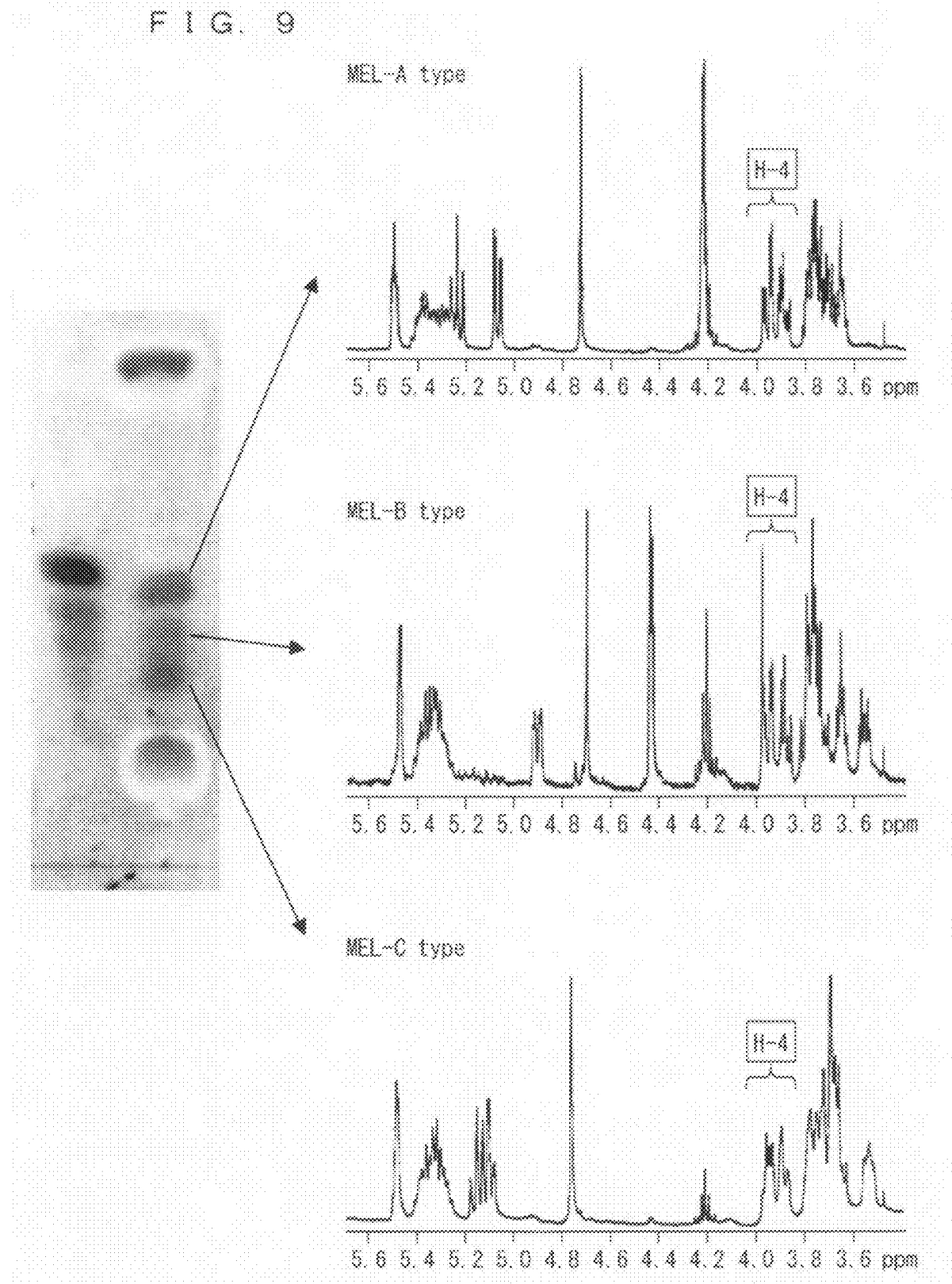
FIG. 9 is an enlarged drawing (3.4-5.7 ppm) of a sugar skeleton part in $^1$H-NMR spectrum of MEL produced by *Pseudozyma crassa* CBS 9959 strain.

Consequently, as illustrated in FIG. 9, it was confirmed that the three kinds of glycolipids produced by *Pseudozyma crassa* CBS 9959 strain correspond to MEL-A, MEL-B, and MEL-C, respectively, and proton at 4-position of erythritol would show two peaks in the conventional MEL, whereas proton at 4-position of erythritol shows one peak in MEL of the present invention. This demonstrated that *Pseudozyma crassa* CBS 9959 strain produced optical isomers, of the respective MEL-A, MEL-B, and MEL-C, where each erythritol was bonded in a manner reverse to the manner of conventional MEL.

Example 14

Comparison of Ability to Form Liquid Crystal

MEL produced by *Pseudozyma tsukubaensis* JCM 10324 strain obtained in Example 8 and conventional MEL produced by *Pseudozyma antarctica* KM-34 (FERMP-20730) strain were compared with each other by a water-invading method in terms of their abilities to form liquid crystal. The result of the comparison shows that MEL derived from *Pseudozyma tsukubaensis* JCM 10324 strain has an ability to form lamella phase in a very wider concentration range than conventional MEL, and is a biosurfactant that is excellent in the ability to form liquid crystal, as illustrated in FIGS. 10 and 11.

Example 15

Production of Triacyl MEL by Culturing *Pseudozyma tsukubaensis* JCM 10324 Strain Frozen stock of 0.2 mL of *P. tsukubaensis* was planted in a 500 ml Sakaguchi flask containing 20 ml of a YM seed medium and cultured at 26° C. at 180 rpm for 1 night to be preinoculum. 0.2 ml of the preinoculum was planted in a 500 ml Sakaguchi flask containing 20 ml of a YM seed medium and cultured at 26° C. at 180 rpm for 1 night to be inoculum. 20 ml of the inoculum was planted in 5 L jar containing 2 L of a YM medium and cultured at 26° C. at 300 rpm (¼VVM, 0.5 L air/min) for 8 days. The culture solution was centrifuged at 7,900 rpm for 60 min at 4° C., so that the culture solution was separated into strain (including MEL-B) and supernatant. 80 ml of ethyl acetate was added to strain fractions, and stirred upward and downward so that the strain was suspended sufficiently, and then centrifuged at 7,900 rpm for 60 min at 4° C. To the obtained supernatant was added the same amount of a saturated saline solution, and the resultant was stirred to obtain an etyl acetate layer. A suitable amount of sulfuric anhydride Na was added to the etyl acetate layer, and left at rest for 30 minutes and then evaporated to obtain glycolipid.

Example 16

NMR Analysis of Triacyl MEL Produced by *Pseudozyma tsukubaensis* JCM 10324

Figure 12:
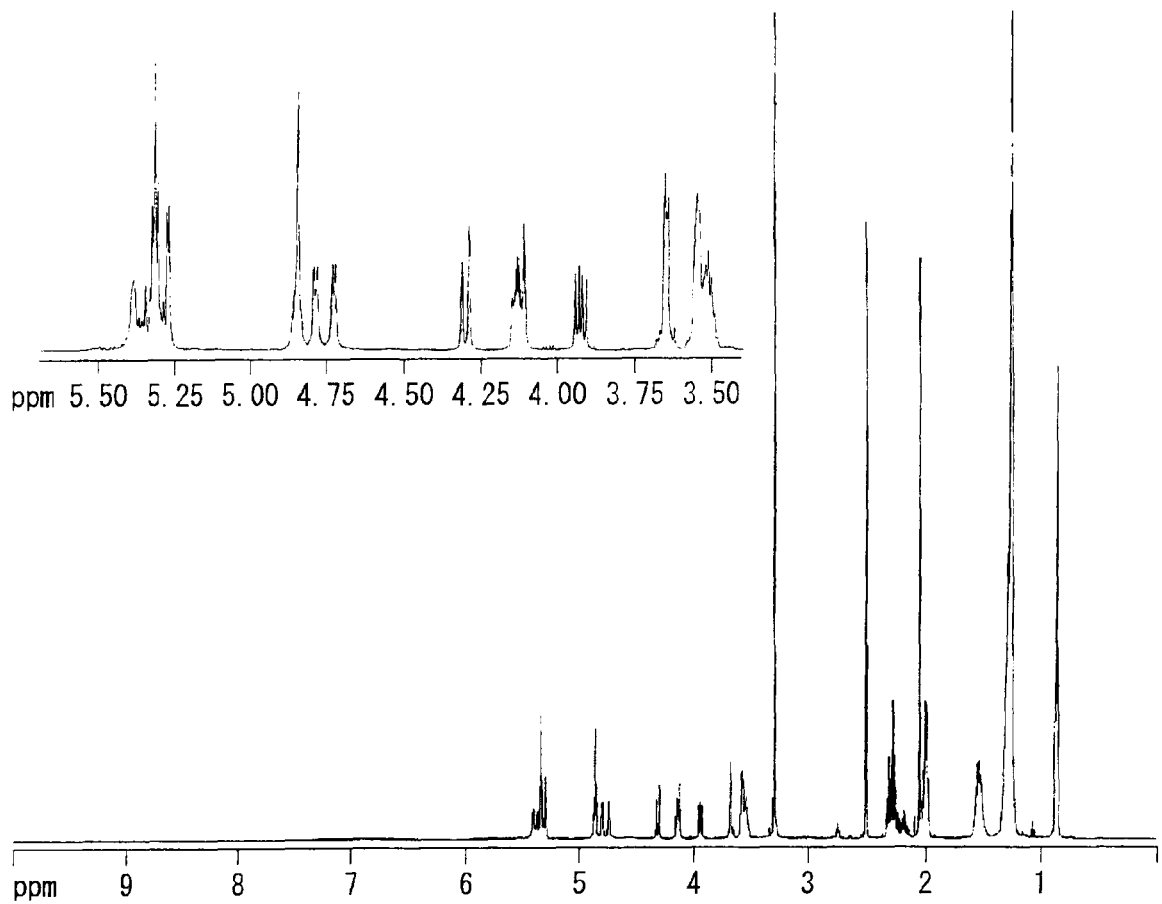
FIG. 12 shows graphs that illustrate $^1$H-NMR spectrum of triacyl MEL produced by *Pseudozyma tsukubaensis* JCM 10324 strain and an enlarged drawing (3.4-5.7 ppm) of a sugar skeleton part in the $^1$H-NMR spectrum, respectively.

Glycolipid obtained in Example 15 was isolated and purified through a known separation method with use of silica gel column chromatography to obtain 50 g of MEL-B and 1.5 g of triacyl MEL-B. Triacyl MEL-B fractions were subjected to $^1$H-NMR analysis with use of deuterated dimethylsulfoxide (DMSO-$d_6$) as a solvent and analyzed in the same manner as that of Example 13. The result is shown in FIG. 12. As shown in FIG. 12, it was confirmed that the triacyl MEL-B produced by *P. tsukubaensis* JCM 10324 strain had erythritol that was bonded in a manner reverse to the manner of conventional MEL.

Figure 13:
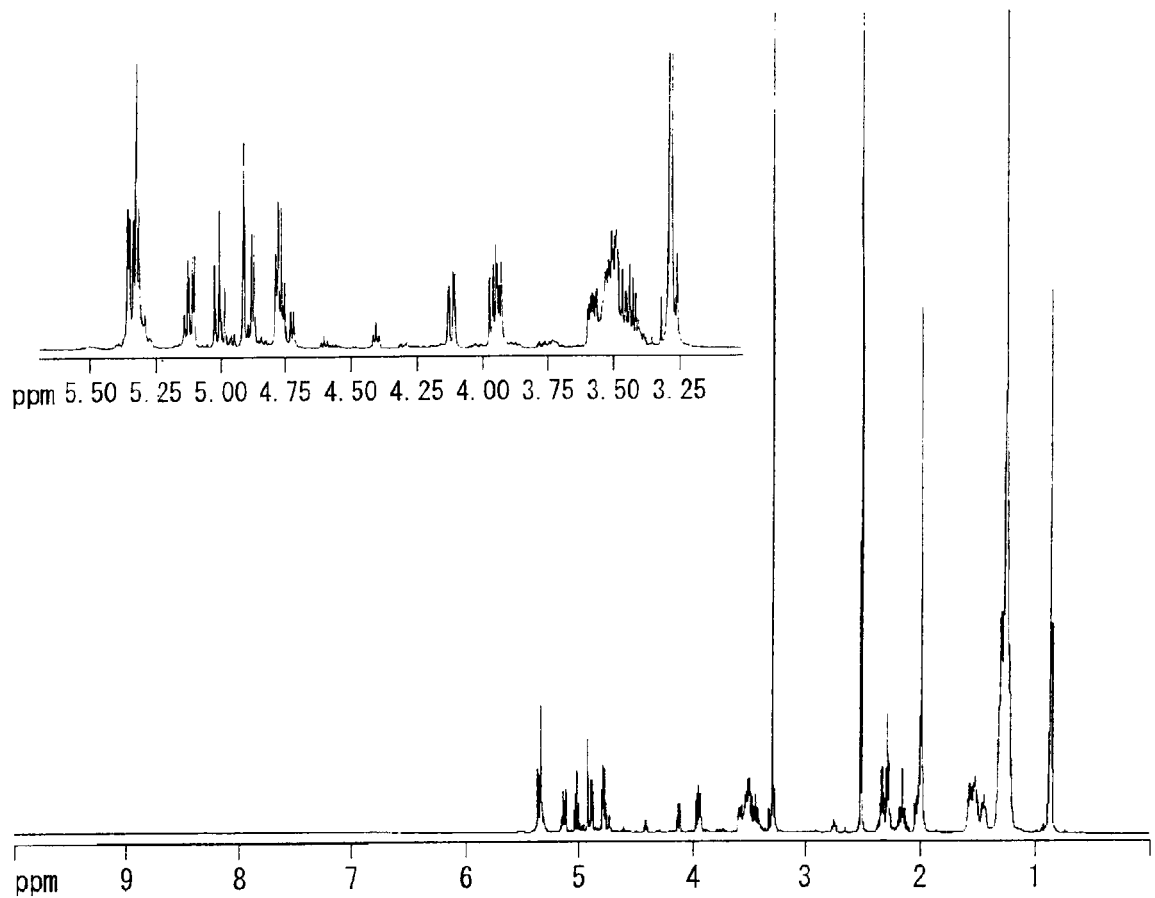
FIG. 13 shows graphs that illustrate $^1$H-NMR spectrum of triacyl MEL produced by *Pseudozyma hubeiensis* and an enlarged drawing (3.0-5.7 ppm) of a sugar skeleton part in the $^1$H-NMR spectrum, respectively.

For comparison, Pseudozyma hubeiensis was cultured and produced, and 45 g of MEL-C and 1.3 g of triacyl MEL-C were isolated and purified with use of silica gel column chromatography in the same manner as above. The triacyl MEL-C was subjected to $^1$H-NMR analysis with use of deuterated dimethylsulfoxide (DMSO-$d_6$) as a solvent. Consequently, as shown in FIG. 13, it was confirmed that MEL-C produced by Pseudozyma hubeiensis had erythritol bonded in the same direction as conventional MEL.

Example 18

Figure 14:
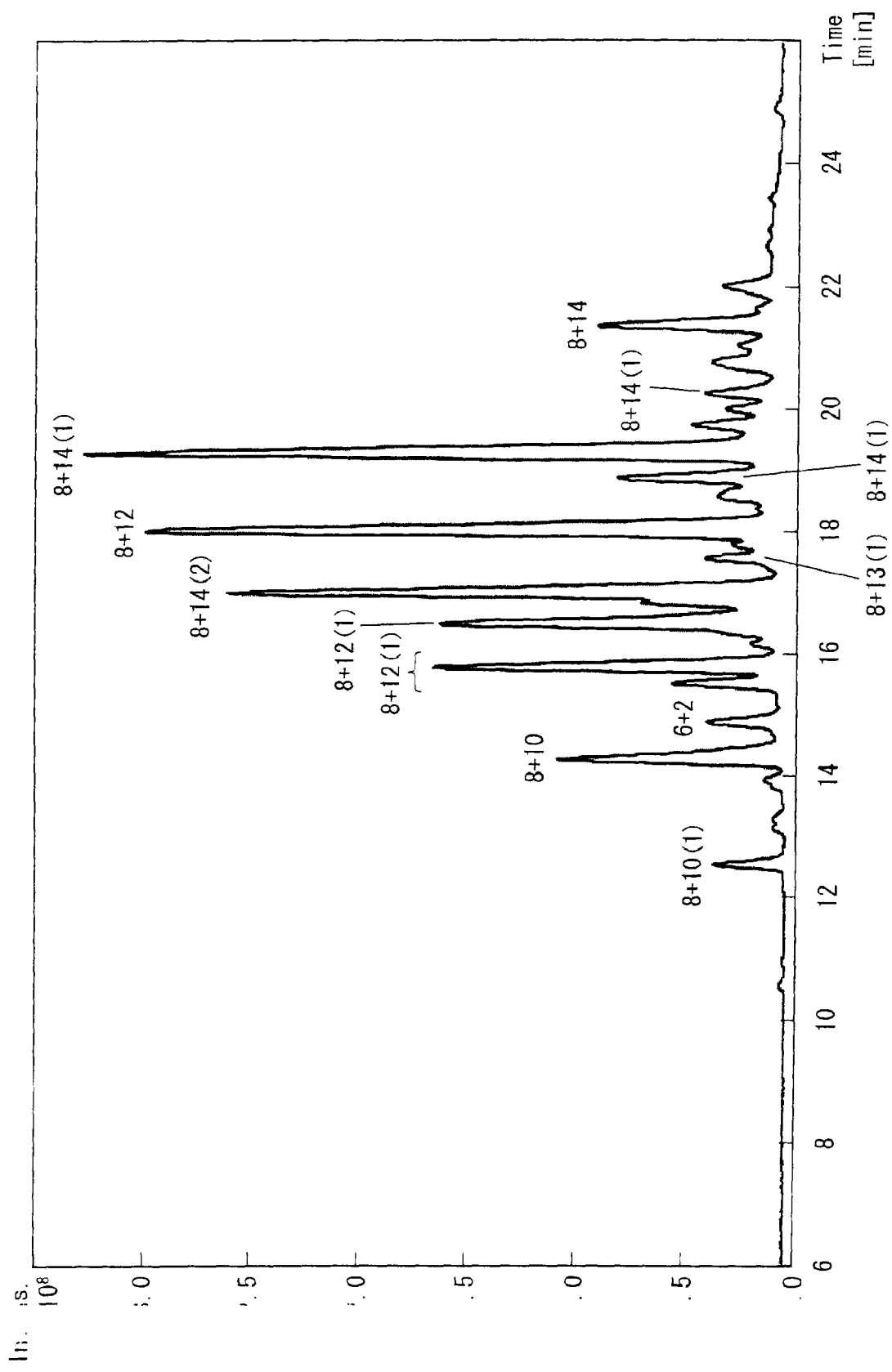
FIG. 14 is a drawing illustrating the result of lipid domain analysis by HPLC (ODS)-MS analysis of MEL produced by *Pseudozyma tsukubaensis* JCM 10324 strain.

Lipid Domain Analysis of MEL-B Produced by *Pseudozyma tsukubaensis* JCM 10324 Strain MEL-B produced by *Pseudozyma tsukubaensis* JCM 10324 strain was separated by high performance liquid chromatography using reverse phase column, and then subjected to mass spectrometry (LC-MS analysis), and a fatty acid structure of lipid domain was confirmed. Consequently, as shown in FIG. 14, it was confirmed that fatty acid having 6 carbon atoms was mainly attached to one hydroxide group of mannose and fatty acid having 10-14 carbon atoms was attached to the other hydroxide group.

As a comparative object, triacyl MEL-C that was produced by culturing *Pseudozyma hubeiensis* and then isolated and purified was subjected to LC-MS analysis in the same manner. Consequently, as shown in FIG. 14, it was confirmed that fatty acid having 6 carbon atoms was mainly attached to one hydroxide group of mannose and fatty acid having 8-16 carbon atoms was attached to the other hydroxide group.

Analysis conditions of HPLC are as follows. HPLC device: Agilent 100, column: Imtakt Cadenza CD-C18 2×150 mm, mobile-phase: A 0.1% formic acid, B acetonitrile, 0 min (50% B)-20 min (98% B)-30 min (98% B), flow rate: 0.2 ml/min, column temperature: 40° C., injection rate: 3 μl. MS conditions are as follows. MS device: BRUKER DALTONICS esquire 3000 Plus, ionization method: ESI positive.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

The present invention provides cosmetics, quasi-drugs (external agent for skin, bath agent, hair growth agent etc.), drinks and foods, and drugs for which highly safe cell-activating function and anti-aging function derived from a biosurfactant can be expected, and which include a cell-activating component and an anti-aging component as active ingredients. Therefore, the present invention is expected to greatly contribute to industries.

Further, the MEL of the present invention has a structure in which erythritol is ether-bonded to mannose in the reverse manner as that of conventional MEL, which makes the MEL of the present invention have an entirely different chilarity, greatly different liquid crystal forming behavior, and a greatly different self-assembling property, from those of the conventional MEL. Because of these differences in the properties, the MEL of the present invention is expected to show new physiological activities that are not seen in the conventional MEL. Therefore, the MEL of the present invention is expected to be widely used in the field of cleaning agents, food industries, chemical industries, environmental fields etc. as the conventional MEL, and in particular greatly contribute to wider application of MEL in the fields such as medicine and cosmetic industries.

The invention claimed is:

1. Mannosylerythritol lipid having a structure represented by formula (1)

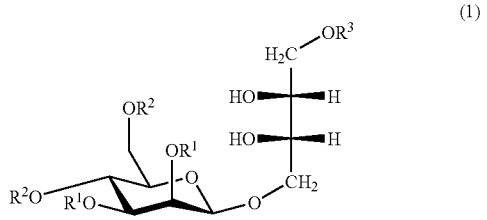

wherein substituents $R^1$ are the same as each other or different from each other and represent fatty series acyl groups having 4-24 carbon atoms, substituents $R^2$ are the same as each other or different from each other and represent hydrogen or acetyl groups, and a substituent $R^3$ represents hydrogen or a fatty series acyl group having 2-24 carbon atoms, excluding a structure wherein the substituents $R^1$ are fatty series acyl groups having 12 carbon atoms, the substituents $R^2$ are acetyl groups, and the substituent $R^3$ is hydrogen.

2. The mannosylerythritol lipid as set forth in claim 1, wherein in the formula (1), one of the substituents $R^2$ is an acetyl group and the other of the substituents $R^2$ is hydrogen.

3. The mannosylerythritol lipid as set forth in claim 1, wherein in the formula (1), the substituent $R^3$ is a fatty series acyl group having 2-24 carbon atoms.

4. The mannosylerythritol lipid as set forth in claim 1, the mannosylerythritol lipid being produced by a microorganism.

5. An activator, comprising as an active ingredient mannosylerythritol lipid as set forth in claim 1.

6. An external agent, comprising as an active ingredient an activator as set forth in claim 5.

7. A cosmetic, comprising as an active ingredient an activator as set forth in claim 5.

8. A method for producing mannosylerythritol lipid, comprising the step of culturing a microorganism that belongs to Pseudozyma genus and that is capable of producing mannosylerythritol lipid, so as to produce mannosylerythritol lipid having a structure represented by formula (1)

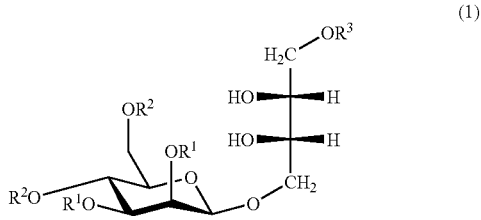

wherein substituents $R^1$ are the same as each other or different from each other and represent fatty series acyl groups having 4-24 carbon atoms, substituents $R^2$ are the same as each other or different from each other and represent hydrogen or acetyl groups, and a substituent $R^3$ represents hydrogen or a fatty series acyl group having 12 carbon atoms.

9. The method as set forth in claim 8, wherein the microorganism is one of *Pseudozyma tsukubaensis* and *Pseudozyma crassa*.

* * * * *